United States Patent
MacLeod et al.

(12)

(10) Patent No.: US 6,211,219 B1
(45) Date of Patent: Apr. 3, 2001

(54) AMINOCYCLOHEXANE DERIVATIVES AS 5-HT RECEPTOR AGONISTS

(75) Inventors: Angus Murray MacLeod, Bishops Stortford; Graham Andrew Showell, Welwyn Garden City; Leslie Joseph Street, Harlow, all of (GB)

(73) Assignee: Merck Sharp & Dohme Ltd., Hertfordshire (GB)

( * ) Notice: Subject to any disclaimer, the term of this patent is extended or adjusted under 35 U.S.C. 154(b) by 0 days.

(21) Appl. No.: 09/214,343

(22) PCT Filed: Jul. 15, 1997

(86) PCT No.: PCT/GB97/01897

§ 371 Date: Jan. 4, 1999

§ 102(e) Date: Jan. 4, 1999

(87) PCT Pub. No.: WO98/03504

PCT Pub. Date: Jan. 29, 1998

(30) Foreign Application Priority Data

Jul. 23, 1996 (GB) .................................................. 9615449

(51) Int. Cl.⁷ ..................... C07D 403/06; A61K 31/4196
(52) U.S. Cl. ...................... 514/383; 548/266.4; 548/255; 546/268.4; 514/339

(58) Field of Search ........................ 514/383; 548/266.4, 548/255

(56) References Cited

FOREIGN PATENT DOCUMENTS

| WO 96/04274 | 2/1996 | (WO) . |
| WO 96/17842 | 6/1996 | (WO) . |
| WO 97/16445 | 5/1997 | (WO) . |

OTHER PUBLICATIONS

CA 119:49144, Hyun et al., 1993.*

* cited by examiner

*Primary Examiner*—Jane Fan
(74) *Attorney, Agent, or Firm*—James L. McGinnis; David L. Rose; Philippe L. Durette

(57) ABSTRACT

A class of substituted aminocyclohexane derivatives are selective agonists of $5\text{-}HT_1$-like receptors, being potent agonists of the human $5\text{-}HT_{1D^\alpha}$ receptor subtype while possessing at least a 10-fold selective affinity for the $5\text{-}HT_{1D^\alpha}$ receptor subtype relative to the $5\text{-}HT_{1D^\beta}$ subtype; they are therefore useful in the treatment and/or prevention of clinical conditions, in particular migraine and associated disorders, for which a subtype-selective agonist of $5\text{-}HT_{1D}$ receptors is indicated, while eliciting fewer side-effects, notably adverse cardiovascular events, than those associated with non-subtype-selective $5\text{-}HT_{1D}$ receptor agonists.

10 Claims, No Drawings

AMINOCYCLOHEXANE DERIVATIVES AS 5-HT RECEPTOR AGONISTS

The present invention relates to a class of substituted aminocyclohexane derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988. Vol. 1, 1309–11; and W. Feniuk and P. P. A. Humphrey, *Drug Development Research*, 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D_\alpha}$ (or 5-HT$_{1D-1}$) and 5-HT$_{1D_\beta}$ (or 5-HT$_{1D-2}$), and their amino acid sequences are disclosed and claimed in WO-A-91/17174.

The 5-HT$_{1D_\alpha}$ receptor subtype in humans is believed to reside on sensory terminals in the dura mater. Stimulation of the 5-HT$_{1D_\alpha}$ subtype inhibits the release of inflammatory neuropeptides which are thought to contribute to the headache pain of migraine. The human 5-HT$_{1D_\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.*, 1992, 304, 1415; J. P. Ottervanger et al., *The Lancet*, 1993, 341, 861–2; and D. N. Bateman, *The Lancet*, 1993, 341, 221–4). Since sumatriptan barely discriminates between the human 5-HT$_{1D_\alpha}$ and 5-HT$_{1D_\beta}$ receptor subtypes (cf. WO-A-91/17174, Table 1), and since it is the blood vessels with which the 5-HT$_{1D_\beta}$ subtype is most closely associated, it is believed that the cardiovascular side-effects observed with sumatriptan can be attributed to stimulation of the 5-HT$_{1D_\beta}$ receptor subtype. It is accordingly considered (cf G. W. Rebeck et al., *Proc. Natl. Acad. Sci. USA*, 1994, 91, 3666–9) that compounds which can interact selectively with the 5-HT$_{1D_\alpha}$ receptor subtype, whilst having a less pronounced action at the 5-HT$_{1D_\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D_\alpha}$ receptor subtype. Moreover, the compounds in accordance with this invention have been found to possess at least a 10-fold selective affinity for the 5-HT$_{1D_\alpha}$ receptor subtype relative to the 5-HT$_{1D_\beta}$ subtype, and they can therefore be expected to manifest fewer side-effects than those associated with non-subtype-selective 5-HT$_{1D}$ receptor agonists.

Several distinct classes of substituted five-membered heteroaromatic compounds are described in published European patent applications 0438230, 0494774 and 0497512, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the substituted aminocyclohexane derivatives provided by the present invention.

WO-A-94/08993 and WO-A-95/28400 describe substituted pyridinyl-benzofuran derivatives, and analogues thereof. These compounds are stated therein to be selective agonists at 5-HT$_1$-like receptors and thus useful in treating conditions associated with cephalic pain, including migraine. Neither of these publications, however, discloses or even suggests the substituted aminocyclohexane derivatives provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the substituted piperazine moiety with a differently substituted cyclohexane moiety.

WO-A-91/18897 describes a class of tryptamine derivatives substituted by various five-membered rings, which are stated to be specific to a particular type of "5-HT$_1$-like" receptor and thus to be effective agents for the treatment of clinical conditions, particularly migraine, requiring this activity. A further class of tryptamine derivatives with alleged anti-migraine activity is disclosed in WO-A-94/02460. However, neither WO-A-91/18897 nor WO-A-94/02460 discloses or suggests the substituted aminocyclohexane derivatives provided by the present invention.

Moreover, nowhere in the prior art mentioned above is there any disclosure of a subtype-selective 5-HT$_{1D}$ receptor agonist having a 5-HT$_{1D_\alpha}$ receptor binding affinity (IC$_{50}$) below 50 nM and at least a 10-fold selective affinity for the 5-HT$_{1D_\alpha}$ receptor subtype relative to the 5-HT$_{1D_\beta}$ subtype.

WO-A-95/32196, WO-A-96/04269, WO-A-96/04274, WO-A-96/16056 and WO-A-96/17842 describe various classes of heterocyclic compounds as alpha subtype-selective agonists of the human 5-HT$_{1D}$ receptor. However, there is no disclosure nor any suggestion in any of these publications of the substituted aminocyclohexane derivatives provided by the present invention.

The compounds according to the present invention are subtype-selective 5-HT$_{1D}$ receptor agonists having a human 5-HT$_{1D_\alpha}$ receptor binding affinity (IC$_{50}$) below 100 nM, typically below 50 nM, suitably below 10 nM and preferably below 1 nM; and at least a 10-fold selective affinity, typically at least a 20-fold selective affinity, suitably at least a 50-fold selective affinity and preferably at least a 100-fold selective affinity, for the human 5-HT$_{1D_\alpha}$ receptor subtype relative to the 5-HT$_{1D_\beta}$ subtype. Moreover, the compounds in accordance with this invention possess interesting properties in terms of their efficacy and/or bioavailability.

The present invention provides a compound of formula I, or a salt or prodrug thereof:

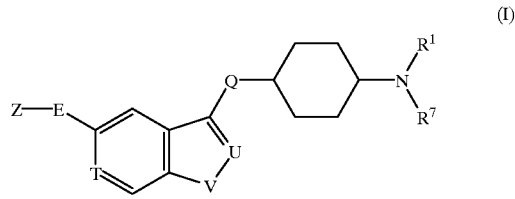

(I)

wherein

Z represents hydrogen, halogen, cyano, nitro, trifluoromethly. —OR$^5$, —OCOR$^5$, —OCONR$^5$R$^6$, —OCH$_2$CN, —OCH$_2$CONR$^5$R$^6$, —SR$^5$, —SOR$^5$, —SO$_2$R$^5$, —SO$_2$NR$^5$R$^6$, —NR$^5$R$^6$, —NR$^5$COR$^6$, —NR$^5$CO$^6$, —NR$^5$SO$_2$R$^6$, —COR$^5$, —CO$_2$R$^5$, —CONR⁵R⁶, or a group of formula (Za), (Zb), (Zc) or (Zd):

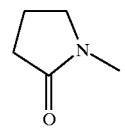
(Za)

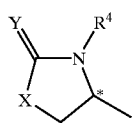
(Zb)

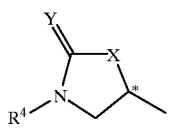
(Zc)

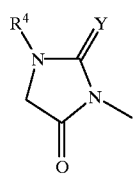
(Zd)

in which the asterisk * denotes a chiral centre; or

Z represents an optionally substituted five-membered herteroaromatic ring selected from furan, thiophene, pyrrole, oxazole, thiazole, isoxazole, isothiazole, imidazole, pyrazole, oxadiazole, thiadiazole, triazole and tetrazole; or Z represents an optionally substituted six-membered heteroaromatic ring selected from pyridine, pyrazine, pyrimidine and pyridazine;

X represents oxygen, sulphur, —NH— or methylene;

Y represents oxygen or sulphur;

E represents a chemical bond or a straight or branched alkylene chain containing from 1 to 4 carbon atoms;

Q represents a straight or branched alkylene chain containing from 1 to 6 carbon atoms, optionally substituted in any position by one or more substituents selected from fluoro and hydroxy;

T represents nitrogen or CH;

U represents nitrogen or C—R²;

V represents oxygen, sulphur or N—R³;

R¹ represents aryl($C_{1-6}$)alkyl, heteroaryl($C_{1-6}$)alkyl or tetrahydronaphthyl, any of which groups may be optionally substituted;

R², R³, R⁴ and R⁷ independently represent hydrogen or $C_{1-6}$ alkyl; and

R⁵ and R⁶ independently represent hydrogen, $C_{1-6}$ alkyl, trifluoromethyl, phenyl, methylphenyl, or an optionally substituted aryl($C_{1-6}$)alkyl or heteroaryl($C_{1-6}$)alkyl group; or R⁵ and R⁶, when linked through a nitrogen atom, together represent the residue of an optionally substituted azetidine, pyrrolidine, piperidine, morpholine or piperazine ring.

The present invention also provides a compound of formula I as depicted above, or a salt or prodrug thereof, wherein R¹ represents aryl($C_{1-6}$)alkyl or heteroaryl($C_{1-6}$)alkyl, either of which groups may be optionally substituted; and Z, E, Q, T, U, V and R⁷ are as defined above.

Where Z in the compounds of formula I above represents a five-membered heteroaromatic ring, this ring may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring as specified for Z include $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano and trifluoromethyl.

Where Z in the compounds of formula I above represents a six-membered heteroaromatic ring, this ring may be optionally substituted by one or more substituents, typically by one or two substituents. Examples of suitable substituents on the six-membered heteroaromatic ring as specified for Z include $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, halogen, halo($C_{1-6}$)alkyl, cyano, cyano($C_{1-6}$)alkyl, trifluoromethyl, and —(CH$_2$)$_a$—R⁸, in which a is zero, 1, 2 or 3 (preferably zero or 1) and R⁸ represents —OR$^a$, —OCOR$^c$, —OCO$_2$R$^a$, —SR$^a$, —SOR$^a$, —SO$_2$R$^c$, —CH=CHSO$_2$R$^c$, —SO$_2$NR$^a$R$^b$, —CH=CHSO$_2$NR$^a$R$^b$, —NR$^a$R$^b$, —NR$^a$COR$^c$, —NR$^a$CO(CH$_2$)$_b$OR$^d$ (in which b is 1 or 2, preferably 1), —NR$^a$CO$_2$R$^d$, —NR$^a$SO$_2$R$^c$, —NR$^d$CONR$^a$R$^b$, —NR$^d$SO$_2$NR$^a$R$^b$, —COR$^c$, —CH=CHCOR$^c$, —CO$_2$R$^a$, —CONR$^a$R$^b$, —CH=CHCONR$^a$R$^b$, or —CONR$^d$NR$^a$R$^b$, or R⁸ represents a group of formula (a), (b), (c), (d) or (e):

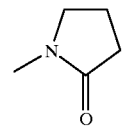
(a)

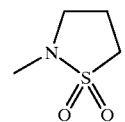
(b)

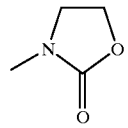
(c)

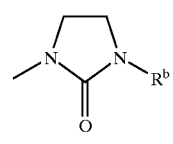
(d)

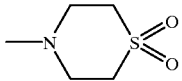
(e)

wherein R$^a$ and R$^d$ independently represent hydrogen, $C_{1-6}$ alkyl, trifluoromethyl, phenyl, fluorophenyl or tetrahydropyranyl; R$^b$ represents hydrogen, $C_{1-6}$ alkyl, trifluoromethyl, phenyl or fluorophenyl; and R$^c$ represents hydrogen, $C_{1-6}$ alkyl, trifluoromethyl, phenyl, fluorophenyl, tetrahydropyranyl, azetidinyl, pyrrolidinyl, piperidinyl or morpholinyl.

The group $R^1$ may be optionally substituted by one or more substituents, as also may the groups $R^5$ or $R^6$ where these represent aryl($C_{1-6}$)alkyl or heteroaryl($C_{1-6}$)alkyl. Where $R^1$, $R^5$ or $R^6$ represents aryl($C_{1-6}$)alkyl or heteroaryl ($C_{1-6}$)alkyl, any optional substitution will suitably be on the aryl or heteroaryl moiety thereof, although substitution on the alkyl moiety thereof is an alternative possibility. Examples of optional substituents thereon include halogen, cyano, trifluoromethyl, triazolyl, tetrazolyl, $C_{1-6}$ alkyl-tetrazolyl, hydroxy, keto, $C_{1-6}$ alkoxy, $C_{1-6}$ alkylthio, $C_{2-6}$ alkoxycarbonyl, $C_{2-6}$ alkylcarbonyl, $C_{1-6}$ alkylsulphonyl, arylsulphonyl, amino, $C_{1-6}$ alkylamino, di($C_{1-6}$)alkylamino, di($C_{1-6}$)alkylaminomethyl, $C_{2-6}$ alkylcarbonylamino, arylcarbonylamino, $C_{2-6}$ alkoxycarbonylamino, N-($C_{1-6}$) alkyl-N-($C_{2-6}$)alkoxycarbonylamino, $C_{1-6}$ alkylsulphonylamino, arylsulphonylamino, $C_{1-6}$ alkylsulphonylaminomethyl, aminocarbonylamino, $C_{1-6}$ alkylaminocarbonylamino, di($C_{1-6}$) alkylaminocarbonylamino, mono- or diarylaminocarbonylamino, pyrrolidinylcarbonylamino, piperidinylcarbonylamino, aminocarbonyl, $C_{1-6}$ alkylaminocarbonyl, di($C_{1-6}$)alkylaminocarbonyl, aminosulphonyl, $C_{1-6}$ alkylaminosulphonyl, di($C_{1-6}$) alkylaminosulphonyl, aminosulphonylmethyl, $C_{1-6}$ alkylaminosulphonylmethyl and di($C_{1-6}$) alkylaminosulphonylmethyl.

When $R^5$ and $R^6$, when linked through a nitrogen atom, together represent the residue of an azetidine, pyrrolidine, piperidine, morpholine or piperazine ring, this ring may be unsubstituted or substituted by one or more substituents. Examples of suitable substituents include $C_{1-6}$ alkyl, aryl ($C_{1-6}$)alkyl, $C_{1-6}$ alkoxy, $C_{2-6}$ alkoxycarbonyl and $C_{1-6}$ alkylaminocarbonyl. Typical substituents include methyl, benzyl, methoxy, methoxycarbonyl, ethoxycarbonyl and methylaminocarbonyl. In particular, where $R^5$ and $R^6$ together represent the residue of a piperazine ring, this ring is preferably substituted on the distal nitrogen atom by a $C_{2-6}$ alkoxycarbonyl moiety such as methoxycarbonyl or ethoxycarbonyl.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$ alkoxy", "$C_{1-6}$ alkylthio" and "$C_{1-6}$ alkylamino" are to be construed accordingly.

The expression "$C_{2-6}$ alkenyl" as used herein refers to straight-chained and branched alkenyl groups containing from 2 to 6 carbon atoms. Typical examples include vinyl, allyl, dimethylallyl and butenyl groups.

The expression "$C_{2-6}$ alkynyl" as used herein refers to straight-chained and branched alkynyl groups containing from 2 to 6 carbon atoms. Typical examples include ethynyl and propargyl groups.

Typical $C_{3-7}$ cycloalkyl groups include cyclopropyl, cyclobutyl, cyclopentyl and cyclohexyl.

Typical $C_{3-7}$ cycloalkyl($C_{1-6}$)alkyl groups include cyclopropylmethyl and cyclohexylmethyl.

Typical aryl groups include phenyl and naphthyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl and morpholinyl groups.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, benzofurylmethyl, thienylmethyl, thienylethyl, indolylmethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Certain compounds according to the present invention may be capable of existing as tautomeric forms. For example, a hydroxypyridine derivative in accordance with the invention may exist in admixture with its tautomeric pyridone isomer. It is to be understood that all possible tautomers and mixtures thereof in any proportion are encompassed within the scope of the present invention.

Where the compounds according to the invention have at least one symmetric centre, they may accordingly exist as enantiomers. Where the compounds according to the invention possess two or more asymmetric centres, they may additionally exist as diastereoisomers. For example, the relative stereochemistry between the Q and —NR$^1$R$^7$ moieties at positions 1 and 4 of the cyclohexane ring in the compounds of formula I as depicted above may be cis or trans, preferably cis. Moreover, the compounds of formula I above wherein Z represents a group of formula (Zb) or (Zc) have a chiral centre denoted by the asterisk *, which may accordingly be in the (R) or (S) configuration. It is to be understood that all such isomers and mixtures thereof in any proportion are encompassed within the scope of the present invention.

Where E and Q, which may be the same or different, represent straight or branched alkylene chains, these may be, for example, methylene, ethylene, 1-methylethylene, propylene, 2-methylpropylene or butylene. In addition, the alkylene chain Q may be substituted in any position by one or more substituents selected from fluoro and hydroxy giving rise, for example, to a 2-hydroxypropylene, 2-hydroxymethylpropylene, 2-fluoropropylene or 2-fluoromethyl-propylene chain Q. Moreover, E may represent a chemical bond such that the moiety Z is attached directly to the central fused bicyclic heteroaromatic ring system containing the variables T, U and V.

Suitably, E represents a chemical bond or a methylene linkage.

Suitably, Q represents an ethylene or propylene linkage, preferably ethylene.

The compound of formula I in accordance with the present invention is suitably an indole, benzofuran or benzthiophene derivative of formula IA, an indazole derivative of formula IB, or a pyrrolo[2,3-c]pyridine derivative of formula IC:

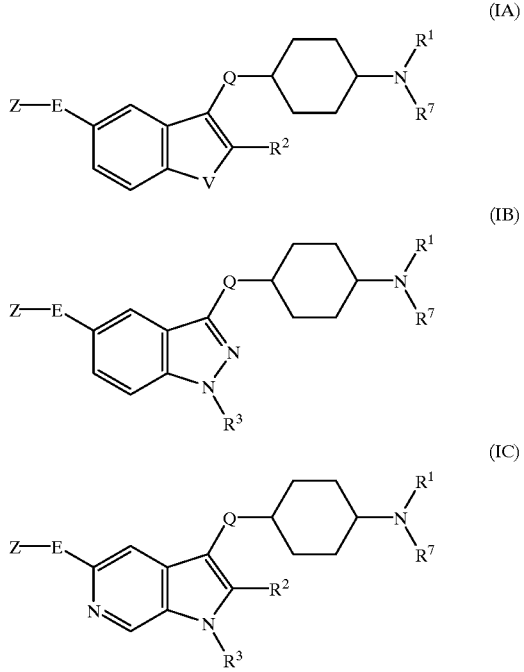

wherein Z, E, Q, V, $R^1$, $R^2$, $R^3$ and $R^7$ are as defined above. Typically, the compounds according to the invention are indole or benzofuran derivatives of formula ID:

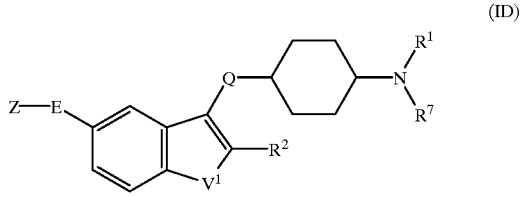

wherein $V^1$ represents oxygen or N—$R^3$, preferably N—$R^3$, and Z, E, Q, $R^1$, $R^2$, $R^3$ and $R^7$ are as defined above, in particular wherein $R^2$ and $R^3$ are both hydrogen.

Typical values for the substituent $R^1$ include benzyl, phenylethyl, phenylpropyl, furylmethyl, benzofurylmethyl, thienylmethyl, indolylmethyl, imidazolylmethyl, pyridinyl-methyl and tetrahydronaphthyl, any of which groups may be substituted by one or more substituents. Suitable values for the substituent $R^1$ include benzyl, phenylethyl, phenylpropyl, furylmethyl, thienylmethyl, imidazolylm-ethyl and pyridinylmethyl, any of which groups may be optionally substituted by one or more substituents.

Examples of typical substituents on the group $R^1$ include halogen, cyano, trifluoromethyl, triazolyl, tetrazolyl, $C_{1-6}$ alkyl-tetrazolyl, hydroxy, keto, $C_{1-6}$ alkoxy, amino, di($C_{1-6}$) alkylamino, di($C_{1-6}$)alkylaminomethyl, $C_{2-6}$ alkylcarbonylamino, $C_{2-6}$ alkoxycarbonylamino, N-($C_{1-6}$) alkyl-N-($C_{2-6}$)alkoxycarbonylamino, $C_{1-6}$ alkylsulphonylamino, aminocarbonylamino, aminocarbonyl, $C_{1-6}$ alkylaminocarbonyl, di($C_{1-6}$) alkylaminocarbonyl, aminosulphonyl and $C_{1-6}$ alkylaminosulphonylmethyl, especially halogen or hydroxy.

Representative values of $R^1$ include benzyl, fluorobenzyl, difluorobenzyl, cyanobenzyl, trifluoromethyl-benzyl, tetrazolyl-benzyl, methyltetrazolyl-benzyl, methoxybenzyl, aminobenzyl, dimethylaminomethyl-benzyl, acetylamino-benzyl, aminocarbonyl-benzyl, methylaminocarbonyl-benzyl, dimethylaminocarbonyl-benzyl, aminosulphonyl-benzyl, 1-phenylethyl, 2-phenylethyl, fluoro-phenylethyl, difluoro-phenylethyl, cyano-phenylethyl, trifluoromethyl-phenylethyl, triazolyl-phenylethyl, 2-hydroxy-1-phenylethyl, 2-hydroxy-2-phenylethyl, phenylcarbonylmethyl, amino-phenylethyl, dimethylamino-p henylethyl, acetylamino-phenylethyl, methoxycarbonylamino-phenn ethyl, (N-methyl-N-methoxycarbonyl)amino-phenylethyl, aminocarbonylamino-phenylethyl, 2-phenylpropyl, 3-phenylpropyl, 2-(fluorophenyl)propyl, 1-phenylprop-2-yl, furylmethyl, benzofuryl-methyl, thienylmethyl, indolylmethyl, imidazolylmethyl, pyridinylmethyl, amino-pyridinylmethyl and tetrahydronaphthyl.

Particular values of $R^1$ include benzyl, fluorobenzyl, 1-phenylethyl, 2-phenylethyl, 2-hydroxy-1-phenylethyl, 2-hydroxy-2-phenylethyl, 2-phenylpropyl, 2-(fluorophenyl) propyl, 1-phenylprop-2-yl, benzofurylmethyl, indolylmethyl, pyridinylmethyl and tetrahydronaphthyl; especially benzyl, fluorobenzyl, 1-phenylethyl, 2-phenylpropyl, 2-(fluorophenyl)propyl and pyridinylm-ethyl.

Suitably, $R^2$ and $R^3$ independently represent hydrogen or methyl, especially hydrogen.

Suitably, $R^4$ represents hydrogen or methyl.

Suitably, $R^5$ and $R^6$ are independently selected from hydrogen, methyl, ethyl, n-propyl, isopropyl, n-butyl, tert-butyl, trifluoromethyl, phenyl, methylphenyl (especially 4-methylphenyl), benzyl and phenethyl.

Suitably, $R^7$ represents hydrogen or methyl, especially methyl.

Suitably, the substituent Z represents hydrogen, fluoro, cyano, hydroxy, methoxy, ethoxy, benzyloxy, methylamino-carbonyloxy, cyano-methoxy, aminocarbonyl-methoxy, methylsulphonyl, aminosulphonyl, N-methylamino-sulphonyl, N,N-dimethylamino-sulphonyl, amino, formylamino, acetylamino, trifluoromethyl-carbonylamino, benzyloxycarbonylamino, methyl-sulphonylamino, ethyl-sulphonylamino, methylphenyl-sulphonylamino, N-methyl-(N-methylsulphonyl)-amino, N-methyl-(N-ethylsulphonyl)-amino, N-methyl-(N-trifluoromethylsulphonyl)-amino, N-ethyl-(N-methylsulphonyl)-amino, N-benzyl-(N-methylsulphonyl)-amino, N-benzyl-(N-ethylsulphonyl)-amino, acetyl, methoxycarbonyl, ethoxycarbonyl, aminocarbonyl, methylaminocarbonyl, ethylaminocarbonyl, propylaminocarbonyl, butylaminocarbonyl, benzylami-nocarbonyl or phenethyl-aminocarbonyl; or a group of formula (Za), (Zb), (Zc) or (Zd) as defined above; or an optionally substituted five-membered or six-membered het-eroaromatic ring as specified above.

In a particular embodiment, Z represents —SO$_2$NR$^5$R$^6$ in which R$^5$ and R$^6$ are as defined above. In a subset of this embodiment, R$^5$ and R$^6$ independently represent hydrogen or C$_{1-6}$ alkyl, especially hydrogen or methyl. Particular values of Z in this context include aminosulphonyl, N-methylamino-sulphonyl and N,N-dimethylamino-sulphonyl, especially N-methylamino-sulphonyl.

In another embodiment, Z represents a group of formula (Zb) in which R$^4$ is hydrogen or methyl. In a subset of this embodiment, X and Y both represent oxygen. In a particular aspect of this subset, the chiral centre denoted by the asterisk * is in the (S) configuration.

When the group Z represents an optionally substituted five-membered heteroaromatic ring, this is suitably a 1,3-oxazole, 1,3-thiazole, imidazole, 1,2,4-oxadiazole, 1,3,4-oxadiazole, 1,2,4-thiadiazole, 1,3,4-thiadiazole, 1,2,3-triazole, 1,2,4-triazole or tetrazole ring. Preferably, the ring is a 1,3-oxazole, 1,3-thiazole, imidazole, 1,2,4-oxadiazole, 1,2,4-thiadiazole or 1,2,4-triazole ring, in particular an imidazol-1-yl, 1,2,4-triazol-1-yl or 1,2,4-triazol-4-yl moiety.

Suitably, the five-membered heteroaromatic ring as specified for Z is unsubstituted. Examples of optional substituents which may typically be attached to the moiety Z include methyl, ethyl, benzyl and amino.

When the group Z represents an optionally substituted six-membered heteroaromatic ring, this is suitably a pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyridazin-3-yl or pyridazin-4-yl ring, especially pyridin-3-yl or pyrimidin-5-yl.

The six-membered heteroaromatic ring as specified for Z is unsubstituted or substituted by one or more substituents, typically by one or two substituents. Examples of optional substituents which may typically be attached to the moiety Z include methyl, methoxy, methoxycarbonyl, methoxymethyl, aminomethyl, dimethylaminomethyl, acetylaminomethyl, benzoylaminomethyl, tert-butoxycarbonylaminomethyl, methylsulphonylaminomethyl, phenylsulphonylaminomethyl, aminocarbonylmethyl, ethyl, aminoethyl, acetylaminoethyl, benzoylaminoethyl, methoxycarbonylaminoethyl, ethoxycarbonylaminoethyl, tert-butoxycarbonylaminoethyl, methylsulphonylaminoethyl, aminocarbonylaminoethyl, methylaminocarbonylaminoethyl, tert-butylaminocarbonylaminoethyl, phenylaminocarbonylaminoethyl, pyrrolidinylcarbonylaminoethyl, cyclopropyl, phenyl, naphthyl, benzyl, phenylethyl, phenylpropyl, pyridinylmethyl, amino, methylamino, dimethylamino, aminocarbonyl, methylaminocarbonyl, azetidinylcarbonyl and pyrrolidinylcarbonyl.

A particular sub-class of compounds according to the invention is represented by the compounds of formula II, and salts and prodrugs thereof:

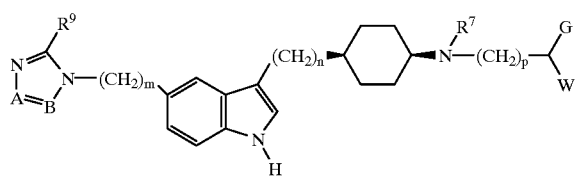

(II)

wherein
    m is zero, 1, 2 or 3, preferably zero or 1;
    n is 2, 3 or 4, preferably 2;
    p is zero, 1 or 2;
    A represents nitrogen or CH;
    B represents nitrogen or C—R$^{10}$;
    R$^7$ is as defined with reference to formula I above:
    R$^9$ and R$^{10}$ independently represent hydrogen, C$_{1-6}$ alkyl, C$_{2-6}$ alkenyl, C$_{3-7}$ cycloalkyl, aryl, aryl(C$_{1-6}$)alkyl, C$_{3-7}$ heterocycloalkyl, heteroaryl, heteroaryl(C$_{1-6}$)alkyl, C$_{1-6}$ alkoxy, C$_{1-6}$ alkylthio, amino, C$_{1-6}$ alkylamino, di(C$_{1-6}$)alkylamino, halogen, cyano or trifluoromethyl;
    G represents hydrogen, hydroxy, C$_{1-3}$ alkyl or hydroxy(C$_{1-3}$)alkyl; and
    W represents a group of formula (Wa), (Wb), (Wc) or (Wd):

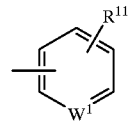

(Wa)

(Wb)

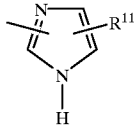

(Wc)

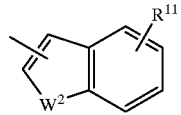

(Wd)

in which
    W$^1$ represents CH or nitrogen;
    W$^2$ represents oxygen, sulphur, NH or N-methyl; and
    R$^{11}$ represents hydrogen, halogen, cyano, trifluoromethyl, triazolyl, tetrazolyl, C$_{1-6}$ alkyl-tetrazolyl, C$_{1-6}$ alkoxy, C$_{2-6}$ alkylcarbonyl, amino, C$_{1-6}$ alkylamino, di(C$_{1-6}$)alkylamino, di(C$_{1-6}$)alkylaminomethyl, C$_{2-6}$ alkylcarbonylamino, C$_{1-6}$ alkylsulphonylamino, aminocarbonylamino, C$_{1-6}$ alkylaminocarbonyl, aminosulphonyl or C$_{1-6}$ alkylaminosulphonylmethyl.

Particular values of R$^9$ and R$^{10}$ include hydrogen, methyl, ethyl, benzyl and amino, especially hydrogen.

Particular values of R$^{11}$ include hydrogen, fluoro, cyano, trifluoromethyl, triazolyl, tetrazolyl, methyl-tetrazolyl, methoxy, amino, dimethylaminomethyl, acetylamino, aminocarbonylamino, methylaminocarbonyl and aminosulphonyl, especially hydrogen or fluoro.

Particular values of G include hydrogen, hydroxy, methyl and hydroxymethyl, typically hydrogen or methyl.

In relation to formula (Wd), the moiety W$^2$ suitably represents oxygen or NH.

In one aspect, the moiety W represents a group of formula (Wa), (Wb) or (Wc) as defined above.

Suitably, W represents a group of formula (Wa).

Suitably, W$^1$ represents CH.

Specific compounds within the scope of the present invention include:

cis-[N-benzyl-N-methyl-N-(4-(2-(5-(1,2,4-triazol-4-yl)-1H-indol-3-yl)ethyl)cyclohex-1-yl)]amine;
cis-[N-benzyl-N-methyl-N-(4-(3-(5-(1,2,4-triazol-4-yl)-1H-indol-3-yl)propyl)cyclohex-1-yl)]amine;
cis-[N-methyl-N-(1-phenylethyl)-N-(4-(2-(5-(1,2,4-triazol-4-yl)-1H-indol-3-yl)ethyl)cyclohex-1-yl)]amine;
cis-[N-(3-fluorobenzyl)-N-methyl-N-(4-(2-(5-(1,2,4-triazol-4-yl)-1H-indol-3-yl)ethyl)cyclohex-1-yl)]amine;
cis-[N-methyl-N-(pyridin-2-ylmethyl)-N-(4-(2-(5-(1,2,4-triazol-4-yl)-1H-indol-3-yl)ethyl)cyclohex-1-yl)]amine;
cis-[N-methyl-N-(2-(RS)-phenylpropyl)-N-(4-(2-(5-(1,2,4-triazol-4-yl)-1H-indol-3-yl)ethyl)cyclohex-1-yl)]amine;
cis-[N-methyl-N-(2-(RS)-phenylpropyl)-N-(4-(3-(5-(1,2,4-triazol-4-yl)-1H-indol-3-yl)propyl)cyclohex-1-yl)]amine;
cis-[N-(2-(RS)-(4-fluorophenyl)propyl)-N-methyl-N-(4-(2-(5-(1,2,4-triazol-4-yl)-1H-indol-3-yl)ethyl)cyclohex-1-yl)]amine;
cis-[N-methyl-N-(pyridin-3-ylmethyl)-N-(4-(2-(5-(1,2,4-triazol-4-yl)-1H-indol-3-yl)ethyl)cyclohex-1-yl)]amine;
cis-[N-(1H-indol-3-ylmethyl)-N-methyl-N-(4-(2-(5-(1,2,4-triazol-4-yl)-1H-indol-3-yl)ethyl)cyclohex-1-yl)]amine;
cis-[N-(benzofuran-3-ylmethyl)-N-methyl-N-(4-(2-(5-(1,2,4-triazol-4-yl)-1H-indol-3-yl)ethyl)cyclohex-1-yl)]amine;
cis-[N-methyl-N-(2-phenylethyl)-N-(4-(2-(5-(1,2,4-triazol-4-yl)-1H-indol-3-yl)ethyl)cyclohex-1-yl)]amine;
cis-[N-(2-(RS)-1-phenylprop-2-yl)-N-(4-(2-(5-(1,2,4-triazol-4-yl)-1H-indol-3-yl)ethyl)cyclohex-1-yl)]amine;
cis-2-[N-methyl-N-(4-(2-(5-(1,2,4-triazol-4-yl)-1H-indol-3-yl)ethyl)cyclohex-1-yl)amino]-1-(RS)-phenylethanol;
cis-[N-benzyl-N-(4-(2-(5-(1,2,4-triazol-4-yl)-1H-indol-3-yl)ethyl)cyclohex-1-yl)]amine;
cis-[N-(2-(RS)-1,2,3,4-tetrahydronaphth-2-yl)-N-(4-(2-(5-(1,2,4-triazol-4-yl)-1H-indol-3-yl)ethyl)cyclohex-1-yl)]amine;
cis-[N-methyl-N-(2-(RS)-1,2,3,4-tetrahydronaphth-2-yl)-N-(4-(2-(5-(1,2,4-triazol-4-yl)-1H-indol-3-yl)ethyl)cyclohex-1-yl)]amine;
cis-[N-(2-(RS)-phenylpropyl)-N-(4-(2-(5-(1,2,4-triazol-4-yl)-1H-indol-3-yl)ethyl)cyclohex-1-yl)]amine;
cis-[N-methyl-N-(2-(RS)-1-phenylprop-2-yl)-N-(4-(2-(5-(1,2,4-triazol-4-yl)-1H-indol-3-yl)ethyl)cyclohex-1-yl)]amine;
trans-2(R)-phenyl-2-[4-(2-(5-(1,2,4-triazol-4-yl)-1H-indol-3-yl)ethyl)cyclohexylamino]ethanol;
trans-2(S)-phenyl-2-[4-(2-(5-(1,2,4-triazol-4-yl)-1H-indol-3-yl)ethyl)cyclohexylamino]ethanol;
cis-2-[N-methyl-N-[4-(2-(5-(1,2,4-triazol-4-yl)-1H-indol-3-yl)ethyl)cyclohexyl]amino]-2(R)-phenylethanol;
cis-2-[N-methyl-N-[4-(2-(5-(1,2,4-triazol-4-yl)-1H-indol-3-yl)ethyl)cyclohexyl]amino]-2(S)-phenylethanol;
trans-2-[N-methyl-N-[4-(2-(5-(1,2,4-triazol-4-yl)-1H-indol-3-yl)ethyl)cyclohexyl]amino]-2(S)-phenylethanol;
and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention wherein T represents CH, U represents C—$R^2$ and V represents N—$R^3$, corresponding to the indole derivatives of formula ID as defined above wherein $V^1$ represents N—$R^3$, may be prepared by a process which comprises reacting a compound of formula III:

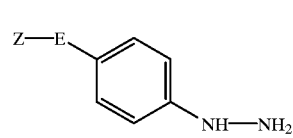

(III)

wherein Z and E are as defined above; with a compound of formula IV, or a carbonyl-protected form thereof:

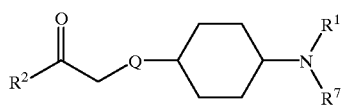

(IV)

wherein $R^1$, $R^2$, $R^7$ and Q are as defined above; followed, where required, by N-alkylation by standard methods to introduce the moiety $R^3$.

The reaction between compounds III and IV, which is an example of the well-known Fischer indole synthesis, is suitably carried out by heating the reagents together under mildly acidic conditions, e.g. 4% sulphuric acid at reflux.

Suitable carbonyl-protected forms of the compounds of formula IV include the dimethyl acetal or ketal derivatives, and the $C_{1-4}$ alkyl enol ether derivatives thereof.

The Fischer reaction between compounds III and IV may be carried out in a single step, or may proceed via an initial non-cyclising step at a lower temperature to give an intermediate of formula V:

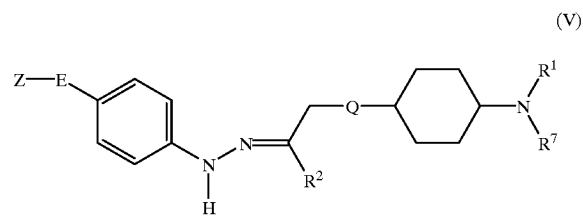

(V)

wherein Z, E, Q, $R^1$, $R^2$ and $R^7$ are as defined above; followed by cyclisation using a suitable reagent, e.g. a polyphosphate ester.

In another procedure, the compounds according to the invention wherein E represents a chemical bond may be prepared by reacting a compound of formula VI with a compound of formula VII:

Z—$M^1$ (VI)

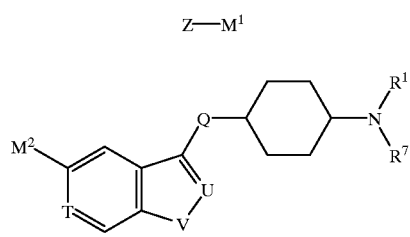

(VII)

wherein Z, Q, T, U, V, $R^1$ and $R^7$ are as defined above; one of $M^1$ and $M^2$ represents a suitable leaving group, and the other represents a boronic acid moiety —$B(OH)_2$ or a $C_{1-4}$ alkyl ester or anhydride thereof; in the presence of a transition metal catalyst.

The leaving group $M^1$ or $M^2$ is suitably a halogen atom, e.g. bromine.

The transition metal catalyst of use in the reaction between compounds VI and VII is suitably tetrakis(triphenylphosphine)palladium(0). The reaction is conveniently carried out in an inert solvent such as aqueous 1,2-dimethoxyethane, advantageously in the presence of a base such as sodium acetate or sodium carbonate, typically at an elevated temperature.

In a further procedure, the compounds according to the invention wherein T represents CH, U represents nitrogen and V represents N—$R^3$, corresponding to the indazole derivatives of formula IB as defined above, may be prepared by a process which comprises cyclising a compound of formula VIII:

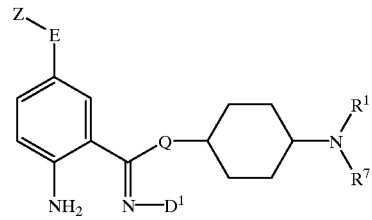

(VIII)

wherein Z, E, Q, $R^1$ and $R^7$ are as defined above, and $D^1$ represents a readily displaceable group; followed, where required, by N-alkylation by standard methods to introduce the moiety $R^3$.

The cyclisation of compound VIII is conveniently achieved in a suitable organic solvent at an elevated temperature, for example in a mixture of m-xylene and 2,6-lutidine at a temperature in the region of 140° C.

The readily displaceable group $D^1$ in the compounds of formula VIII suitably represents a $C_{1-4}$ alkanoyloxy group, preferably acetoxy. Where $D^1$ represents acetoxy, the desired compound of formula VIII may be conveniently prepared by treating a carbonyl compound of formula IX:

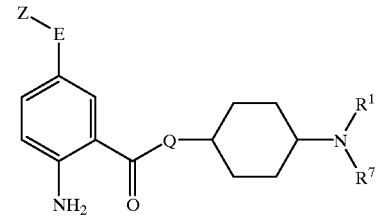

(IX)

wherein Z, E, Q, $R^1$ and $R^7$ are as defined above; or a protected derivative thereof, preferably the N-formyl protected derivative; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula IX may conveniently be prepared by ozonolysis of the corresponding indole derivative of formula X:

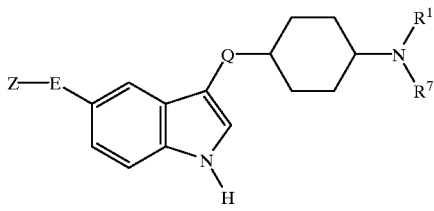

(X)

wherein Z, E, Q, $R^1$ and $R^7$ are as defined above; followed by a reductive work-up, advantageously using dimethylsulphide.

The indole derivatives of formula X may be prepared by methods analogous to those described in the accompanying Examples, or by procedures well known from the art.

In a still further procedure, the compounds according to the invention wherein T represents CH, U represents C—$R^2$ and V represents oxygen or sulphur, corresponding to the benzofuran or benzthiophene derivatives of formula IA wherein V is oxygen or sulphur respectively, may be prepared by a process which comprises cyclising a compound of formula XI:

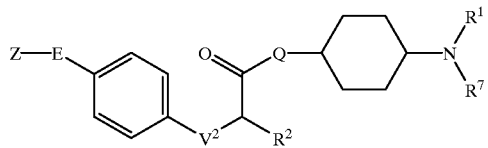

(XI)

wherein Z, E, Q, $R^1$, $R^2$ and $R^7$ are as defined above, and $V^2$ represents oxygen or sulphur.

The cyclisation of compound XI is conveniently effected by using polyphosphoric acid or a polyphosphate ester, advantageously at an elevated temperature.

The compounds of formula XI may be prepared by reacting a compound of formula XII with a compound of formula XIII:

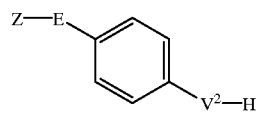

(XII)

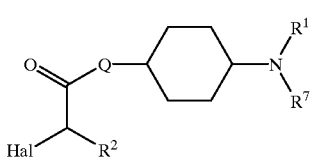

(XIII)

wherein Z, E, Q, $R^1$, $R^2$, $R^7$ and $V^2$ are as defined above, and Hal represents a halogen atom.

The reaction is conveniently effected in the presence of a base such as sodium hydroxide.

The hydroxy and mercapto derivatives of formula XII may be prepared by a variety of methods which will be readily apparent to those skilled in the art. One such method is described in EP-A-0497512.

In a yet further procedure, the compounds according to the invention may be prepared by a process which comprises attachment of the $R^1$ moiety to a compound of formula XIV:

(XIV)

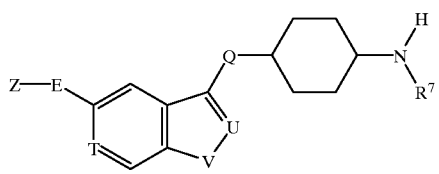

wherein Z, E, Q, T, U, V and $R^7$ are as defined above; by conventional means including N-alkylation.

A typical N-alkylation technique for attachment of the desired $R^1$ moiety comprises reductive alkylation using the appropriate aldehyde or ketone in the presence of a reducing agent such as sodium cyanoborohydride or sodium triacetoxyborohydride, typically in acetic acid and methanol or dichloromethane at room temperature. Another typical N-alkylation technique for attachment of the desired $R^1$ moiety comprises displacement of the halogen atom from a compound of formula $R^1$-halide, e.g. 1-bromoethylbenzene, in the presence of a base such as potassium carbonate, typically in a solvent such as N,N-dimethylformamide at an elevated temperature.

The intermediates of formula XIV above wherein $R^7$ is hydrogen may be prepared by deprotection of a compound of formula XV:

(XV)

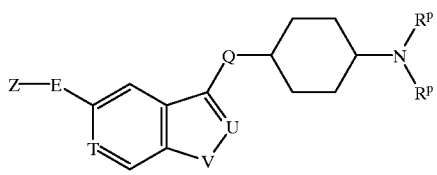

wherein Z, E, Q, T, U and V are as defined above, and $R^P$ represents an amino-protecting group.

The amino-protecting group $R^P$ in the compounds of formula XV is suitably benzyl, in which case the deprotection can conveniently be effected as necessary by conventional catalytic hydrogenation procedures.

In an additional procedure, the compounds according to the invention may be prepared by a process which comprises reacting a compound of formula XVI with a compound of formula XVII:

(XVI)

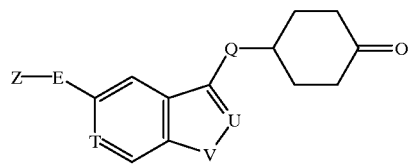

(XVII)

wherein Z, E, Q, T, U, V, $R^1$ and $R^7$ are as defined above; in the presence of a reducing agent.

A suitable reducing agent for use in the reaction between compounds XVI and XVII is sodium cyanoborohydride, in which case the reaction is conveniently carried out in acetic acid and methanol.

The intermediates of formula XVI above may be prepared by oxidation of a compound of formula XVIII:

(XVIII)

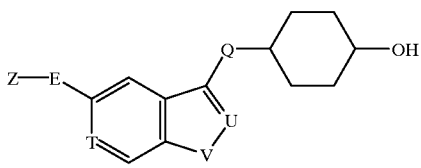

wherein Z, E, Q, T, U and V are as defined above.

A suitable oxidising agent for effecting this transformation is sulphur trioxide pyridine complex, in which case the reaction is conveniently carried out under basic conditions, e.g. triethylamine, in a suitable solvent such as dimethyl sulphoxide.

The intermediates of formula XV and XVIII above correspond to the compounds of formula I above in which the —NR$^1$R$^7$ moiety has been replaced by —N(R$^P$)$_2$ and —OH respectively. These intermediates malt therefore be prepared by methods analogous to those described above for the preparation of the corresponding compounds of formula I.

The hydrazine derivatives of formula III above may be prepared by methods analogous to those described in EP-A-0438230, EP-A-0497512, EP-A-0548813 and WO-A-91/18897.

Where they are not commercially available, the starting materials of formula IV, VI, VII, XIII and XVII may be prepared by methods analogous to those described in the accompanying Examples, or by standard procedures well known from the art.

It will be understood that any compound of formula I initially obtained from any of the above processes may, where appropriate. subsequently be elaborated into a further compound of formula I by techniques known from the art. For example, a compound of formula I wherein R$^1$ is benzyl initially obtained may be debenzvlated by catalytic hydrogenation to afford a compound of formula XIV, and then converted into a further compound of formula I using standard N-alkylation techniques as described above. Moreover, a compound of formula I wherein R$^7$ is hydrogen initially obtained may be converted into a corresponding compound wherein R$^7$ is C$_{1-6}$ alkyl, also using standard N-alkylation techniques. Furthermore, a compound of formula I initially obtained wherein the R$^1$ moiety is substituted by nitro or cyano may be converted by catalytic hydrogenation to the corresponding amino- or aminomethyl-substituted compound respectively. Additionally, a compound of formula I wherein the R$^1$ moiety is substituted by hydroxy, possibly obtained by sodium borohydride reduction of a ketone precursor or by lithium aluminium hydride reduction of a precursor alkoxycarbonyl derivative, may be mesylated under standard conditions, and the mesyl group subsequently displaced by an amino moiety by treatment with the desired amine in a sealed tube at an elevated temperature. The amine derivative resulting from any of these procedures may then, for example, be N-acylated using the appropriate acyl halide, e.g. acetyl chloride; or aminocarbonylated, using potassium isocyanate, to the corresponding urea derivative; or converted to a 1,2,4-triazol-4-yl derivative using N,N-dimethylformamide azine; or reductively alkylated by treatment with the appropriate aldehyde or ketone in the presence of sodium cyanoborohydride. If desired, the amine derivative may also be carbamoylated by treatment with the requisite alkyl chloroformate. A compound of formula I. initially obtained wherein the R$^1$ moiety is substituted by cyano may be converted, by treatment with sodium azide, to the corresponding tetrazole derivative, which in turn may be alkylated on the tetrazole ring by treatment with an alkyl halide under standard conditions. By way of additional illustration, a compound of formula I initially obtained wherein the R$^1$ moiety is substituted by an alkoxycarbonyl moiety may be saponified, by treatment with an alkali metal hydroxide, to the corresponding carboxy-substituted compound, which in turn may be converted to an amide derivative by treatment with the appropriate amine, advantageously in the presence of 1-(3-dimethylaminopropyl)-3-ethylcarbodiimide hydrochloride and 1-hydroxybenzotriazole. Moreover, a compound of formula I wherein R$^3$ is hydrogen initially obtained may be converted into a compound of formula I wherein R$^3$ represents C$_{1-6}$ alkyl by standard alkylation techniques, for example by treatment with an alkyl iodide, e.g. methyl iodide, typically under basic conditions, e.g. sodium hydride in N,N-dimethylformamide.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (-)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the 5-HT$_{1D_\alpha}$ receptor subtype, inhibit forskolin-stimulated adenylyl cyclase activity, and stimulate [$^{35}$S]-GTPγS binding to membranes from clonal cell lines expressing human cloned receptors.

5-HT$_{1D_\alpha}$/5-HT$_{1D_\beta}$ Radioligand Binding

Chinese hamster ovary (CHO) clonal cell lines expressing the human 5-HT$_{1D_\alpha}$ and 5-HT$_{1D_\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM:

Tris-HCl 50, pargyline 0.01, CaCl$_2$ 4; ascorbate 0.1%; pH 7.7 at room temperature) to give the required volume immediately prior to use (0.2 mg protein/ml). Incubations were carried out for 30 min at 37° C. in the presence of 0.02–150 nM [$^3$H]-5-HT for saturation studies or 2–5 nM [$^3$H]-5-HT for displacement studies. The final assay volume was 1 ml. 5-HT (10 μM) was used to define non-specific binding. The reaction was initiated by the addition of membrane and was terminated by rapid filtration through Whatman GF/B filters (presoaked in 0.3% PEI/0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which IC$_{50}$ (the molar concentration of compound necessary to inhibit binding by 50%) values could be calculated for each test compound. The IC$_{50}$ values for binding to the 5-HT$_{1D_\alpha}$ receptor subtype obtained for the compounds of the accompanying Examples were below 100 nM in each case. Furthermore, the compounds of the accompanying Examples were all found to possess a selective affinity for the 5-HT$_{1D_\alpha}$ receptor subtype of at least 10-fold relative to the 5-HT$_{1D_\beta}$ subtype.

5-HT$_{1D_\alpha}$/5-HT$_{1D_\beta}$ Adenylyl Cyclase Assay

Studies were performed essentially as described in *J. Pharmacol. Exp. Ther.*, 1986, 238, 248. CHO clonal cell lines expressing the human cloned 5-HT$_{1D_\alpha}$ and 5-HT$_{1D_\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of α-[$^{33}$P]-ATP to [$^{33}$P]-cyclic AMP. A 10 μl aliquot of the membrane suspension was incubated, for 10–15 min, in a final volume of 50 μl, at 30° C., with or without forskolin (10 μM), in the presence or absence of test compound. The incubation buffer consisted of 50 mM Tris HCl (pH 7.6 at room temperature), 100 mM NaCl, 30 μM GTP, 50 μM cyclic AMP, 1 mM dithiothreitol, 1 mM ATP, 5 mM MgCl$_2$, 1 mM EGTA, 1 mM 3-isobutyl-1-methylxanthine, 3.5 mM creatinine phosphate, 0.2 mg/ml creatine phosphokinase, 0.5–1 μCi α-[$^{33}$P]-ATP and 1 nCi [$^3$H]-cyclic AMP. The incubation was initiated by the addition of membrane, following a 5 min preincubation at 30° C., and was terminated by the addition of 100 μl SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which E$_{max}$ (maximal effect) and EC$_{50}$ (the molar concentration of compound necessary to inhibit the maximal effect by 50%) values were obtained for each test compound. Of those compounds which were tested in this assay, the EC$_{50}$ values for the 5-HT$_{1D_\alpha}$ receptor obtained for the compounds of the accompanying Examples were below 500 nM in each case. Moreover, the compounds of the accompanying Examples which were tested were all found to possess at least a 10-fold selectivity for the 5-HT$_{1D_\alpha}$ receptor subtype relative to the 5-HT$_{1D_\beta}$ subtype.

5-HT$_{1D_\alpha}$/5-HT$_{1D_\beta}$ GTPγS Binding

Studies were performed essentially as described in *Br. J. Pharmacol.*, 1993, 109, 1120. CHO clonal cell lines expressing the human cloned 5-HT$_{1D_\alpha}$ and 5-HT$_{1D_\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–2.5 minutes. The membranes were then resuspended in assay buffer (composition in mM: HEPES 20, NaCl 100, MgCl$_2$ 10, pargyline 0.01; ascorbate 0.1%: pH 7.4 at room temperature) at a concentration of 40 μg protein/ml for the 5-HT$_{1D_\alpha}$ receptor transfected cells and 40–50 μg protein/ml for the 5-HT$_{1D_\beta}$ receptor transfected cells. The membrane suspension was then incubated, in a volume of 1 ml, with GDP (100 μM for 5-HT$_{1D_\alpha}$ receptor transfected cells, 30 μM for the 5-HT$_{1D_\beta}$ receptor transfected cells) and test compound at 30° C. for 20 min and then transferred to ice for a further 15 min. [$^{35}$S]-GTPγS was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which Emax (maximal effect) and EC$_{50}$ (the molar concentration of compound necessary to inhibit the maximal effect by 50%) values were obtained for each test compound. Of those compounds which were tested in this assay, the EC$_{50}$ values for the 5-HT$_{1D_\alpha}$ receptor obtained for the compounds of the accompanying Examples were below 500 nM in each case. Moreover, the compounds of the accompanying Examples which were tested were all found to possess at least a 10-fold selectivity for the 5-HT$_{1D_\alpha}$ receptor subtype relative to the 5-HT$_{1D_\beta}$ subtype.

EXAMPLE 1

Cis-[N-Benzyl-N-methyl-N-(4-(2-(5-(1,2,4-triazol-4-yl)-1H-indol-3-yl)ethyl)cyclohex-1-yl)]amine 1.7 Hydrogen Oxalate 1. N-Benzyl-N-(1,4-dioxaspiro[4.5]dec-8-yl)-N-methylamine Hydrogen Oxalate A stirred solution of N-benzylmethylamine (12.4 ml, 0.096 mol) in 1,2-dichloroethane (400 ml) was treated with 1,4-dioxaspiro[4.5]decan-8-one (15 g, 0.096 mmol) and glacial acetic acid (5.5 ml, 0.096 mol). After 15 minutes this solution was treated with sodium triacetoxyborohydride (30.5 g, 0.144 mol) portionwise and the reaction mixture was stirred at ambient temperature for 5 hours. 10% Potassium carbonate solution (200 ml) was added, the organic solvent evaporated and the aqueous was extracted with dichloromethane (3×300 ml). The combined organics were dried (potassium carbonate) and evaporated to give the crude product (31 g) which was purified by column chromatography on silica using dichloromethane/methanol (30:1). The product free base was obtained as a pale pink oil (24.4 g, 97%). MS, ES$^+$, m/z=262 for (M+H)$^+$; δ(250 MHz, CDCl$_3$) 1.50–1.85 (8H, m), 2.20 (3H, s), 2.46–2.60 (1H, m), 3.57 (2H, s), 3.95 (4H, s), 7.18–7.32 (5H, m). The hydrogen oxalate salt had mp. 188–190° C. (Found: C, 61.48; H, 7.21; N, 4.23. C$_{16}$H$_{23}$NO$_2$. C$_2$H$_2$O$_4$ requires C, 61.52; H, 7.17; N, 3.99%).

2. 4-(N-Benzyl-N-methylamino)cyclohexanone

A solution of the foregoing ketal free base (24.3 g, 0.093 mol) in tetrahydrofuran (250 ml) was treated with 2M hydrochloric acid (250 ml) and heated at reflux under an atmosphere of nitrogen for 5 hours. After cooling to room temperature the reaction mixture was basified to pH=10 with 4M sodium hydroxide. The tetrahydrofuran was evaporated and the residue extracted with ethyl acetate (4×250 ml). The combined organics were washed with brine, dried (sodium sulphate) then evaporated to give the crude product as a red oil (22.5 g). The product was purified by column chromatography on silica using ethyl acetate/n-hexane (1:2) to afford the title compound as a yellow oil (14 g, 70%). MS, ES$^+$, m/z=218 for (M+H)$^+$; δ(250 MHz, CDCl$_3$) 1.82–2.15 (4H, m), 2.23 (3H, s), 2.26–2.56 (4H, m), 2.83–2.94 (1H, m), 3.61 (2H, s), 7.21–7.34 (5H, m).

3. E-4-[4-(N-Benzyl-N-methylamino)cyclohexylidene]but-2-enoic acid ethyl ester Hydrogen Oxalate A stirred, cooled (−78° C.) solution of triethyl phosphonocrotonate (24 ml, 0.108 mol) in anhydrous tetrahydrofuran (700 ml), under an atmosphere of nitrogen, was treated with potassium bis(trimethylsilyl)amide (208 ml of a 0.5M toluene solution, 0.104 mol) dropwise over 30 minutes. The dark orange solution was stirred at −78° C. for 7 hours then treated with a solution of 4-(N-benzyl-N-methylamino)

cyclohexanone (14 g, 0.0646 mol) in anhydrous tetrahydrofuran (100 ml). The reaction mixture was stirred whilst warming to room temperature overnight then quenched with saturated ammonium chloride solution (500 ml) and stirred vigorously for 20 minutes. The tetrahydrofuran was evaporated and the aqueous was extracted with ethyl acetate (3×300 ml). The combined organics were dried (magnesium sulphate) then evaporated and the crude product was purified by column chromatography on silica using ethyl acetate/n-hexane (1:2) to afford the title compound free base as a yellow oil (17.3 g, 86%). MS, ES$^+$, m/z=314 for (M+H)$^+$; δ(250 MHz, CDCl$_3$) 1.30 (3H, t, J=7 Hz), 1.38–1.58 (2H, m), 1.90–2.05 (2H, m), 2.12–2.23 (1H, m), overlapped with 2.19 (3H, s), 2.41 (1H, br d, J=14 Hz), 2.63–2.74 (1H, m), 2.98 (1H, br d, J=14 Hz), 3.57 (2H, s), 4.20 (2H, q, J=7 Hz), 5.80 (1H, d, J=15 Hz), 5.95 (1H, d, J=12 Hz), 7.21–7.32 (5H, m), 7.60 (1H, dd, J$_1$=12, J$_2$=15 Hz). The hydrogen oxalate salt had mp. 112–117° C. (Found: C, 65.16; H, 7.23; N, 3.39. C$_{20}$H$_{27}$NO$_2$. C$_2$H$_2$O$_4$ requires C, 65.49; H, 7.25; N, 3.47%).

4. Cis-4-[4-(N-Benzyl-N-methylamino)cyclohexyl]butyric acid ethyl ester Hydrogen Oxalate The foregoing diene free base (8.0 g, 0.025 mol) in ethyl acetate (100 ml) was treated with platinum oxide (600 mg) and stirred at ambient temperature under an atmosphere of hydrogen for 4 hours. The reaction mixture was filtered and the solvent evaporated to give a mixture of cis and trans isomers which were separated by column chromatography using ethyl acetate/n-hexane mixtures to obtain first the cis-isomer as a pale yellow oil (6.13 g, 77%) then the trans-isomer as a pale yellow oil (0.35 g).

Cis-isomer: MS, ES$^+$, m/z=318 for (M+H)$^+$; δ(250 MHz, CDCl$_3$) 1.20 (3H, t, J=7 Hz), 1.25–1.63 (13H, m), 2.08 (3H, s), 2.24 (2H, t, J=7 Hz), 2.28–2.36 (1H, m), 3.48 (2H, s), 4.06 (2H, q, J=7 Hz), 7.13–7.25 (5H, m). The hydrogen oxalate salt had mp 117–118° C. (Found: C, 64.78; H, 8.17; N, 3.40. C$_{20}$H$_{31}$NO$_2$. C$_2$H$_2$O$_4$ requires C, 64.84; H, 8.16; N, 3.44%).

Trans-isomer: MS, ES$^+$, m/z=318 for (M+H)$^+$; δ(250 MHz, CDCl$_3$) 0.82–1.02 (2H, m), 1.17–1.40 (5H, m), overlapped with 1.25 (3H, t, J=7 Hz), 1.52–1.66 (2H, m), 1.78–1.92 (4H, m), 2.19 (3H, s), 2.27 (2H, t, J=7 Hz), 2.42 (1H, dd, J$_1$=J$_2$=12 Hz), 3.56 (2H, s), 4.12 (2H, q, J=7 Hz), 7.22–7.32 (5H, m).

5. Cis-4-[4-(N-Benzyl-N-methylamino)cyclohexyl]butan-1-ol Hydrogen Oxalate

The foregoing cis-cyclohexylbutyric acid ethyl ester (4.7 g, 0.015 mol) in anhydrous toluene (200 ml) was cooled to 0° C. under a nitrogen atmosphere then treated with diisobutylaluminium hydride (37 ml of a 1M toluene solution, 0.037 mol). The mixture was allowed to warm to room temperature then stirred for 2 hours. Methanol (50 ml) was added, followed by saturated potassium carbonate solution (100 ml). The organic layer was separated then the aqueous re-extracted with ethyl acetate. The combined organics were washed with brine, dried (magnesium sulphate) then evaporated to give the crude product (5.1 g). This crude product was purified by column chromatography on silica using 2% methanol in dichloromethane to afford the title compound free base as a yellow oil (3.23 g, 79%). MS, ES$^+$, m/z=276 for (M+H)$^+$; δ(250 MHz, CDCl$_3$) 1.33–1.70 (15H, m), 2.16 (3H, s), 2.34–2.48 (1H, m), 3.57 (2H, s), 3.66 (2H, t, J=7 Hz), 7.21–7.33 (5H, m). The hydrogen oxalate salt had mp 128–130° C. (Found: C, 65.58; H, 8.69; N, 3.80. C$_{18}$H$_{29}$NO. C$_2$H$_2$O$_4$ requires C, 65.73; H, 8.55; N, 3.83%).

6. Cis-4-[4-(N-Benzyl-N-methylamino)cyclohexyl]butyraldehyde

The foregoing alcohol (4.2 g, 0.015 mol) in dimethyl sulphoxide (50 ml) was treated with triethylamine (14 ml) at 5° C. followed by sulphur trioxide pyridine complex (3.67 g, 0.023 mol), portionwise. The mixture was stirred whilst warming to room temperature and stirred for 2 hours. Water (40 ml) was added and the mixture extracted with ethyl acetate (3 times). The combined organics were washed with brine (4 times), dried (sodium sulphate) and evaporated. The crude aldehyde was purified by column chromatography on silica (dry flash-plug column) using ethyl acetate/n-hexane (1:2) to afford the title aldehyde as a yellow oil (3.13 g, 75%). MS, ES$^+$, m/z=274 for (M+H)$^+$; δ(250 MHz, CDCl$_3$) 1.32–1.70 (13H, m), 2.15 (3H, s), 2.36–2.42 (1H, m), overlapped with 2.44 (2H, dt, J$_1$=2, J$_2$=7 Hz), 3.54 (2H, s), 7.20–7.32 (5H, m), 9.78 (1H, t, J=2 Hz).

7. Cis-[N-Benzyl-N-methyl-N-(4-(2-(5-(1,2,4-triazol-4-yl)-1H-indol-3-yl)ethyl)cyclohex-1-yl)]amine 1.7 Hydrogen Oxalate A stirred solution of 4-(1,2,4-triazol-4-yl) phenylhydrazine hydrochloride (2.82 g, 0.0114 mol) in 4% aqueous sulphuric acid (125 ml), at 70° C., was treated dropwise over 1 hour with a solution of cis-4-[4-(N-benzyl-N-methylamino)cyclohexyl]butyraldehyde (3.1 g, 0.0114 mol) in ethanol (50 ml). The reaction mixture was heated at reflux for 6 hours, cooled, evaporated, the residue re-dissolved in 4% aqueous sulphuric acid and heated at reflux for a further 14 hours. The reaction mixture was cooled then evaporated. The residue was basified to pH=10 with aqueous ammonia and the mixture extracted exhaustively with ethyl acetate. The combined organics were evaporated then the residue treated with ethanol to azeotrope off residual water. The resulting brown oil was purified by column chromatography on silica using dichloromethane→5% methanol/dichloromethane to afford the title compound free base as a gum (2.8 g, 59%). The hydrogen oxalate salt had mp>90° C. MS, ES$^+$, m/z=414 for (M+H)$^+$ of free base, δ(500 MHz, d$_6$-DMSO+TFA) 1.48–1.90 (11H, m), 2.62 (3H, d, J=5 Hz, N-Me), 2.72 (2H, t, J=7 Hz, CH$_2$-indole), 3.18–3.24 (1H, m), 4.16 (1H, dd, J$_1$=7, J$_2$=13 Hz, one of PhCH$_2$N), 4.46 (1H, dd, J$_1$=3, J$_2$=13 Hz, one of PhCH$_2$N), 7.32–7.58 (8H, m), 7.95 (1H, d, J=2 Hz), 9.29 (1H, br s, NH$^+$), 9.90 (2H, br s, 2×triazole-H), 11.25 (1H, s, indole-NH). (Found: C, 62.07; H, 6.62; N, 12.20. C$_{26}$H$_{31}$N$_5$. 1.7C$_2$H$_2$O$_4$. 0.2 (C$_2$H$_5$)$_2$O requires C, 62.39; H, 6.31; N, 12.04%).

EXAMPLE 2

Cis-[N-Benzyl-N-methyl-N-(4-(3-(5-(1,2,4-triazol-4-yl)-1H-indol-3-yl)pronyl)cyclohex-1-yl)]amine 1.6 Hydrogen Oxalate 1. Cis-[N-Benzyl-N-[4-(5-methoxypent-4-enyl) cyclohexyl]-N-methyl]amine Hydrogen Oxalate A suspension of (methoxymethyl)triphenyl phosphonium chloride (1.37 g, 4 mmol) in diethyl ether (20 ml) was cooled to 0° C. under a nitrogen atmosphere. Phenyllithium (2.2 ml of a 1.8M cyclohexane-diethyl ether solution) was added. The mixture was warmed to room temperature then stirred for 30 minutes. The mixture was re-cooled to −15° C. then treated with a solution of cis-4-[4-(N-benzyl-N-methylamino)cyclohexyl]butyraldehyde (0.84 g, 3.08 mmol, Example 1, Step 6) in diethyl ether (5 ml). The mixture was allowed to warm to room temperature then stirred for 4 hours, quenched with saturated aqueous ammonium chloride solution, then the diethyl ether layer was collected and the aqueous re-extracted with ethyl acetate (3×30 ml). The combined organics were dried (sodium sulphate) and evaporated. The crude product was purified by column chromatography on silica (dry flash column) using dichloromethane→1% methanol/dichloromethane. The title compound free base (1 g) was converted to its hydrogen oxalate salt. MS, ES$^+$, m/z=302 for (M+H)$^+$ of free base, δ(360 MHz, d$_6$-DMSO) 1.20–2.04 (15H, m), 2.62 (3H, s), 3.14–3.26 (1H, m), 3.52 (3H, s), 4.15 (1H, dd, J$_1$=7, J$_2$=13 Hz), 4.46 (1H, dd, J$_1$=2, J$_2$=13 Hz), 5.96 (1H, d, J=6 Hz), 6.33 (1H, d, J=13 Hz), 7.45–7.66 (5H, m).

2. Cis-[N-Benzyl-N-methyl-N-(4-(3-(5-(1,2,4-triazol-4-yl)-1H-indol-3-yl)propyl)cyclohex-1-yl)]amine 1.6 Hydrogen Oxalate The title compound free base was obtained (32 mg, 7%) from the foregoing enol-ether hydrogen oxalate and 4-(1,2,4-triazol-4-yl)phenylhydrazine hydrochloride as described in Example 1, Step 7. The hydrogen oxalate salt had mp>80° C. MS, ES$^+$, m/z=428 for (M+H)$^+$ of free base, δ(360 MHz, d$_6$-DMSO+TFA) 1.40–1.90 (13H, m), 2.60 (3H, d, J=5 Hz), 2.73 (2H, t, J=7 Hz), 3.14–3.24 (1H, m), 4.15 (1H, dd, J$_1$=7, J$_2$=13 Hz), 4.45 (1H, dd, J$_1$=2, J$_2$=13 Hz), 7.24–7.55 (8H, m), 7.89 (1H, s), 9.30 (1H, br s), 9.67 (2H, s), 11.20 (1H, s). (Found: C, 63.44; H, 7.00; N, 11.67. C$_{27}$H$_{33}$N$_5$. 1.6 C$_2$H$_2$O$_4$.0.3 (C$_2$H$_5$)$_2$O requires C, 63.50; H, 6.65; N, 11.79%).

EXAMPLE 3

Cis-[N-Methyl-N-(1-phenylethyl)-N-(4-(2-(5-(1,2,4-triazol-4-yl)-1H-indol-3-yl)ethyl)cyclohex-1-yl)]amine 2 Hydrogen Oxalate 1. Cis-[N-Methyl-N-(4-(2-(5-(1,2,4-triazol-4-yl)-1H-indol-3-yl)ethyl)cyclohex-1-yl)]amine Hydrogen Oxalate Cis-[N-Benzyl-N-methyl-N-(4-(2-(5-(1,2,4-triazol-4-yl)-1H-indol-3-yl)ethyl)cyclohex-1-yl)]amine (1.4 g, 3.4 mmol, Example 1) in ethanol (30 ml) was treated with 20% palladium hydroxide on carbon (0.7 g) and hydrogenated under a hydrogen atmosphere at 50 psi for 2.5 hours. Further 20% palladium hydroxide on carbon (0.5 g) was added and the mixture hydrogenated for a further 4 hours. Reaction mixture filtered, the ethanol was evaporated to give the title compound free base as a pale yellow oil (0.9 g, 82%). MS, ES$^+$, m/z=324 for (M+H)$^+$, δ(250 MHz, CDCl$_3$) 1.40–1.72 (11H, m), 2.42 (3H, s), 2.56–2.64 (1H, m), 2.76 (2H, t, J=7 Hz), 7.11–7.15 (2H, m), 7.47 (1H, d, J=8 Hz), 7.54 (1H, d, J=2 Hz), 8.48 (2H, s), 8.70 (1H, br s). The hydrogen oxalate salt had mp. >95° C. (Found: C, 57.59; H, 6.63; N, 14.82. C$_{19}$H$_{25}$N$_5$. 1.5C$_2$H$_2$O$_4$. 0.1H$_2$O requires C, 57.41; H, 6.18; N, 15.22).

2. Cis-[N-Methyl-N-(1-phenylethyl)-N-(4-(2-(5-(1,2,4-triazol-4-yl)-1H-indol-3-yl)ethyl)cyclohex-1-yl)]amine 2 Hydrogen Oxalate The foregoing methylamine (150 mg, 0.46 mmol) in dimethyl formamide (10 ml) was treated with potassium carbonate (64 mg, 0.46 mmol) and 1-bromoethylbenzene (85 mg, 0.46 mmol) then stirred at 70° C. under a nitrogen atmosphere for 20 hours. The reaction mixture was cooled, solvent evaporated and the residue partitioned between water and dichloromethane. The organic layer was separated, and the aqueous re-extracted with dichloromethane. The combined organics were dried (potassium carbonate), evaporated and the residue purified by thin-layer preparative silica chromatography using dichloromethane/methanol/ammonia (125:1:0.2) to afford the title compound free base as a gum (25 mg, 13%). The hydrogen oxalate salt had mp >90° C. MS, ES$^+$, m/z=428 for (M+H)$^+$ of free base, δ(360 MHz, d$_6$-DMSO) 1.40–1.54 (2H, m), 1.56 (3H, d, J=7 Hz), 1.60–1.80 (9H, m), 2.73 (2H, t, J=7 Hz), 2.96–3.06 (1H, m), 4.50 (1H, q, J=7 Hz), 7.25–7.53 (8H, m), 7.72 (1H, d, J=2 Hz), 9.02 (2H, s), 11.10 (1H, s). (Found: C, 60.90; H, 6.31; N, 11.58. C$_{27}$H$_{33}$N$_5$. 2 C$_2$H$_2$O$_4$ requires C, 61.27; H, 6.14, N, 11.53%).

EXAMPLE 4

Cis-[N-(3-Fluorobenzyl)-N-methyl-N-(4-(2-(5-(1,2,4-triazol-4-yl)-1H-indol-3-yl)ethyl)cyclohex-1-yl)]amine 1.45 Hydrogen Oxalate Cis-[N-Methyl-N-(4-(2-(5-(1,2,4-triazol-4-yl)-1H-indol-3-yl)ethyl)cyclohex-1-yl)]amine (100 mg, 0.31 mmol, Example 3, Step 1) and 3-fluorobenzaldehyde (38.4 mg, 0.31 mmol) in dichloromethane (10 ml) were treated with glacial acetic acid (0.02 ml, 0.31 mmol) and sodium triacetoxyborohydride (99 mg, 0.47 mmol). The reaction mixture was stirred at room temperature for 3 days, then treated with 10% potassium carbonate solution. The organic layer was separated and the aqueous re-extracted with dichloromethane. The combined organics were dried (potassium carbonate) then evaporated. The crude product was purified by column chromatography on silica (short plug column) using 2% methanol/dichloromethane→7% methanol/dichloromethane to afford the title compound free base (30 mg, 22%) as a pale yellow gum. The hydrogen oxalate salt had mp >85° C. MS, ES$^+$, m/z=432 for (M+H)$^+$ of free base. (Found: C, 59.92; H, 6.30; N, 11.88. C$_{26}$H$_{30}$FN$_5$. 1.45 C$_2$H$_2$O$_4$. 1H$_2$O requires C, 59.83; H, 6.06; N, 12.07%).

EXAMPLE 5

Cis-[N-Methyl-N-(pyridin-2-ylmethyl)-N-(4-(2-(5-(1,2,4-triazol-4-yl)-1H-indol-3-yl)ethyl)cyclohex-1-yl)]amine 2 Hydrogen Oxalate The title compound free base was obtained (80 mg, 62%) as described in Example 4, using 2-pyridinecarboxaldehyde instead of 3-fluorobenzaldehyde. The hydrogen oxalate salt had mp >85° C. MS, ES$^+$, m/z=415 for (M+H)$^+$ of free base. (Found: C, 56.39; H, 6.07; N, 13.40. C$_{25}$H$_{30}$N$_6$. 2C$_2$H$_2$O$_4$. 1H$_2$O requires C, 56.03; H, 6.00; N, 13.52%).

EXAMPLE 6

Cis-[N-Methyl-N-(2-(RS)-phenylpropyl)-N-(4-(2-(5-(1,2,4-triazol-4-yl)-1H-indol-3-yl)ethyl)cyclohex-1-yl)]amine 1.6 hydrogen oxalate and 2.6 citrate salts The title compound free base was obtained (75 mg, 55%) as described in Example 4, using 2-(RS)-phenylpropionaldeliyde instead of 3-fluorobenzaldehyde. The hydrogen oxalate salt had mp >80° C. MS, ES$^+$, m/z=442 for (M+H)$^+$ of free base, δ(360 MHz, d$_6$-DMSO) 1.31 (3H, d, J=6 Hz), 1.35–1.80 (11H, m), 2.61 (3H, s), 2.73 (2H, t, J=7 Hz), 2.94–3.06 (1H, m), 3.15–3.26 (3H, m), 7.19–7.40 (7H, m), 7.49 (1H, d, J=8 Hz), 7.72 (1H, d, J=2 Hz), 8.88 (2H, s). 10.90 (1H, s). (Found: C, 63.79: H, 7.20; N, 11.61. C$_{28}$H$_{35}$N$_5$. 1.6 C$_2$H$_2$O$_4$. 0.3 (C$_2$H$_5$)$_2$O requires C, 64.01; 6.83; N, 11.52%).

The citrate salt had mp >65° C. (Found: C, 55.89; H, 6.70; N, 7.19. C$_{28}$H$_{35}$N$_5$. 2.6 C$_6$H$_8$O$_7$. 0.25 (C$_2$H$_5$)$_2$O requires C, 55.82; H, 6.12; N, 7.30%).

EXAMPLE 7

Cis-[N-Methyl-N-(2-(RS)-phenylpropyl)-N-(4-(3-(5-(1,2,4-triazol-4-yl)-1H-indol-3-yl)propyl)cyclohex-1-yl)]amine Hydrogen Oxalate 1. Cis-[N-Methyl-N-(4-(3-(5-(1,2,4-triazol-4-yl)-1H-indol-3-yl)propyl)-cyclohex-1-yl)]amine formate Cis-[N-Benzyl-N-methyl-N-(4-(3-(5-(1,2,4-triazol-4-yl)-1H-indol-3-yl)propyl)cyclohex-1-yl)]amine (57 mg, 1.70 mmol, Example 2), ammonium formate (53.5 mg, 8.48 mmol), 10% palladium on carbon (57 mg) and formic acid (0.1 ml) were heated at reflux in methanol (10 ml) for 1.5 hours. The mixture was cooled, filtered then evaporated to give the title compound as a pale yellow solid (39 mg). MS, ES$^+$, m/z=338 for (M+H)$^+$ of free base.

2. Cis-[N-Methyl-N-(2-(RS)-phenylpropyl)-N-(4-(3-(5-(1,2,4-triazol-4-yl)-1H-indol-3-yl)propyl)cyclohex-1-yl)]amine Hydrouen Oxalate The foregoing methylamine formate salt (40 mg, 0.10 mmol) in methanol (5 ml) was treated with 2-(RS)-phenylpropionaldehyde (32 mg, 0.12 mmol), glacial acetic acid (1 ml) then sodium cyanoborohydride (15 mg, 0.12 mmol). After stirring at room temperature for 1 day further quantities (as above) of the aldehyde and sodium cyanoborohydride were added. The mixture was stirred at room temperature for 5 days. Saturated potassium carbonate solution was added, the methanol was evaporated and the residue extracted with dichloromethane (3×20 ml). The combined organics were dried (potassium carbonate), evaporated and the residue purified by thin layer preparative chromatography on silica using dichloromethane/methanol (100:1). The title compound free base was obtained (20 mg, 44%) as a gum. The hydrogen oxalate salt had mp >65° C. MS, ES$^+$, m/z=456 for (M+H)$^+$ of free base. R$_f$=0.39 in dichloromethane/methanol/ammonia (9:1:0.1) on silica plates.

EXAMPLE 8

Cis-[N-(2-(RS)-(4-Fluorophenyl)propyl)-N-methyl-N-(4-(2-(5-(1,2,4-triazol-4-yl)-1H-indol-3-yl)ethyl)cyclohex-1-yl)]amine citrate 1. 2-(RS)-(4-Fluorophenyl)propionaldehyde A stirred, cooled (0° C.) solution of methoxymethyltriphenyl phosphonium chloride (40.8 g, 0.119 mol) in anhydrous diethyl ether (600 ml) under a nitrogen atmosphere was treated with phenyllithium (67 ml of a 1.8M cyclohexane-diethyl ether solution, 0.12 mol) over 30 minutes. After a further 30 minutes at 0° C. the mixture was cooled to −15° C. then treated with 4-fluoroacetophenone (15 g, 0.108 mol). After addition the mixture was stirred at −15° C. for 30 minutes then allowed to warm to room temperature overnight. Saturated ammonium chloride solution was added and the organic layer separated. The aqueous was re-extracted with diethyl ether and the combined organics washed with water, dried (magnesium sulphate) and the solvent evaporated. The crude material was purified by column chromatography on silica using n-hexane→1.5% ethyl acetate/n-hexane to afford the enol-ether as an oil (8.94 g, 50%). A cooled (0° C.) solution of this enol-ether (250 mg, 1.5 mmol) in tetrahydrofuran (8 ml) was treated with concentrated hydrochloric acid (1.5 ml), stirred at 0° C. for 30 minutes then at room temperature for 3 hours. The solution was evaporated and the residue partitioned between water (10 ml) and diethyl ether (30 ml). The organic layer was separated and the aqueous re-extracted twice with diethyl ether. The combined organics were washed with water (3 times), dried (magnesium sulphate) and evaporated to give the title compound (250 mg), as an oil, δ(250 MHz, CDCl$_3$) 1.43 (3H, d, J=7 Hz), 3.56–3.74 (1H, m), 6.98–7.36 (4H, m), 9.66 (1H, d, J=1.5 Hz).

2. Cis-[N-(2-(RS)-(4-Fluorophenyl)propyl)-N-methyl-N-(4-(2-(5-(1,2,4-triazol-4-yl)-1H-indol-3-yl)ethyl)cyclohex-1-yl)]amine citrate The title compound free base was obtained (20 mg, 18%) as described in Example 4, using 2-(RS)-(4-fluorophenyl)propionaldehyde. The citrate salt had mp >50° C. MS, ES$^+$, m/z=460 for (M+H)$^+$ of free base, δ(500 MHz, d$_6$-DMSO) 1.24 (3H, d, J=6 Hz), 1.35–1.80 (11H, m), 2.61 (3H, s) overlapped with 2.58–2.70 (m, includes citric acid protons), 2.90–3.05 (1H, m), 3.10–3.30 (m, overlapped with HOD), 7.18 (2H, dd, J$_1$=J$_2$=9 Hz), 7.28–7.31 (2H, m), 7.39–7.42 (2H, m), 7.48 (1H, d, J=9 Hz), 7.76 (1H, d, J=2 Hz), 9.01 (2H, s), 11.07 (1H, s).

EXAMPLE 9

Cis-[N-Methyl-N-(pyridin-3-ylmethyl)-N-(4-(2-(5-(1,2,4-triazol-4-yl)-1H-indol-3-yl)ethyl)cyclohex-1-yl)]amine 2.65 Hydrogen Oxalate The title compound free base was obtained (65 mg, 51%) as described in Example 4, using 3-pyridinecarboxaldehyde instead of 3-fluorobenzaldehyde. The hydrogen oxalate salt had mp >65° C. MS, ES$^+$, m/z=415 for (M+H)$^+$ of free base. (Found: C, 55.53; H, 5.66; N, 13.14. C$_{25}$H$_{30}$N$_6$. 2.65 C$_2$H$_2$O$_4$ requires C, 55.72; H, 5.45; N, 12.87%).

EXAMPLE 10

Cis-[N-(1H-Indol-3-ylmethyl)-N-methyl-N-(4-(2-(5-(1,2,4-triazol-4-yl)-1H-indol-3-yl)ethyl)cyclohex-1-yl)]amine 2 Hydrozen Oxalate A stirred suspension of cis-[N-methyl-N-(4-(2-(5-(1,2,4-triazol-4-yl)-1H-indol-3-yl)ethyl)cyclohexyl)]amine (Example 3, Step 1, 100 mg, 0.31 mmol) in toluene (25 ml) was treated with gramine (54 mg, 0.31 mmol) and the reaction mixture was heated at reflux for 48 hours. The solvent was evaporated and the residue purified by column chromatography on silica using dichloromethane/methanol/ammonia (5:1:0.1) then on neutral alumina (grade 3) using dichloromethane/methanol (19:1) to give the title compound free base as a colourless gum (60 mg, 43%). The hydrogen oxalate salt had mp >105° C. MS, ES$^+$, m/z=453 for (M+H)$^+$ of free base, δ(360 MHz, d$_6$-DMSO) 1.24–2.00 (11H, m), 2.69 (3H, d, J=5 Hz), 2.72 (2H, t, J=6 Hz), 3.20–3.30 (1H, m), 4.34 (1H, dd, J$_1$=6, J$_2$=12 Hz), 4.62 (1H, dd, J$_1$=2, J$_2$=12 Hz), 7.09–7.20 (2H, m), 7.37 (1H, s), 7.41 (1H, d, J=8 Hz), 7.46 (1H, d, J=8 Hz), 7.56 (1H, d, J=8 Hz), 7.61 (1H, d, J=3 Hz), 7.71 (1H, d, J=8 Hz), 7.94 (1H, s), 9.05 (2H, s), 9.48 (1H, s), 11.23 (1H, s), 11.49 (1H, s). (Found: C, 60.62; H, 6.11; N, 13.12. C$_{28}$H$_{32}$N$_6$. 2C$_2$H$_2$O$_4$ requires C, 60.75; H, 5.74; N, 13.28%).

EXAMPLE 11

Cis-[N-(Benzofuran-3-ylmethyl)-N-methyl-N-(4-(2-(5-(1,2,4-triazol-4-yl)-1H-indol-3-yl)ethyl)cyclohex-1-yl)]amine 2.5 Hydrogen Oxalate A solution of 3-hydroxymethylbenzofuran (52 mg, 0.35 mmol, WO 95/29911) in anhydrous diethyl ether (10 ml) was treated with thionyl chloride (0.03 ml, 0.38 mmol) and stirred at room temperature for 2.5 hours then evaporated. The chloromethylbenzofuran produced was dissolved in dimethyl sulphoxide (10 ml), treated with potassium carbonate (86 mg, 0.62 mmol) and a solution of cis-[N-methyl-N-(4-(2-(5-(1,2,4-triazol-4-yl)-1H-indol-3-yl)ethyl) cyclohexyl)]amine (Example 3, Step 1, 100 mg, 0.31 mmol) in dimethyl sulphoxide (100 ml) and the reaction mixture was stirred at 45° C. (oil bath temperature), under a nitrogen atmosphere, for 8 hours. The reaction mixture was poured into water (40 ml) and extracted with 15% methanol in dichioromethane (3×30 ml). The combined organics were washed with water (40 ml), evaporated and the residue purified by plug column chromatography on silica using dichloromethane/methanol (19:1→9:1→6:1) to afford the title compound free base as a beige gum (110 mg, 78%). The hydrogen oxalate salt had mp 115–118° C. MS, ES$^+$, m/z=454 for (M+H)$^+$ of free base, δ(500 MHz, d$_6$-DMSO) 1.40–1.95 (11H, m), 2.68 (3H, s), 2.72 (2H, t, J=7 Hz), 3.00–3.40 (1H, m), 4.45 (2H, br s), 7.29–7.41 (4H, m), 7.48 (1H, d, J=8 Hz), 7.65 (1H, d, J=8 Hz), 7.78 (1H, d, J=2 Hz), 7.86 (1H, d, J=8 Hz), 8.25 (1H, s), 9.02 (2H,s), 11.12 (1H, s). (Found: C, 55.94; H, 5.83; N, 10.21. C$_{28}$H$_{31}$N$_5$O. 2.5C$_2$H$_2$O$_4$. 1.5H$_2$O requires C, 56.17; H, 5.57; N, 9.92%).

EXAMPLE 12

Cis-[N-Methyl-N-(2-phenylethyl)-N-(4-(2-(5-(1,2,4-triazol-4-yl)-1H-indol-3-yl)ethyl)cyclohex-1-yl)] amine 1.5 Hydrogen Oxalate The title compound free base was obtained (35 mg, 26%) as described in Example 3, Step 2, using 2-phenylethyl bromide instead of 1-bromoethylbenzene. The hydrogen oxalate salt had mp >95° C. MS, ES$^+$, m/z=428 for (M+H)$^+$ of free base. (Found: C, 64.02; H, 6.83; N, 12.17. C$_{27}$H$_{33}$N$_5$. 1.5C$_2$H$_2$O$_4$. 0.3 C$_4$H$_{10}$O requires C, 64.07; H, 6.72; N, 11.97%).

EXAMPLE 13

Cis-[N-(2-(RS)-1-Phenylpron-2-yl)-N-(4-(2-(5-(1,2,4-triazol-4-yl)-1H-indol-3-yl)ethyl)cyclohex-1-yl)] amine 1.5 Hydrogen Oxalate 1. N,N-Dibenzyl-N-(1,4-dioxaspiro[4.5]dec-8-yl)amine 1.0 Hydrogen Oxalate The title compound free base was obtained (34 g, 100%) as described in Example 1, Step 1, using dibenzylamine instead of N-benzylmethylamine. The hydrogen oxalate salt had mp >95° C. MS, ES$^+$, m/z=338 for (M+H)$^+$ of free base, δ(360 MHz, d$_6$-DMSO) 1.28–1.38 (2H, m), 1.54–1.74 (4H, m), 1.78–1.86 (2H, m), 2.54–2.64 (1H, m), 3.67 (4H, s), 3.78–3.88 (4H, m), 7.20–7.36 (10H, m). (Found: C, 62.39; H, 6.74; N, 3.28. C$_{22}$H$_{27}$NO$_2$. 1.0C$_2$H$_2$O$_4$. 1.75H$_2$O requires C, 62.80; H, 7.13; N, 3.05%).

2. 4-(N,N-Dibenzylamino)cyclohexanone 1.15 Hydrogen Oxalate

The title compound free base was obtained (10 g, 81%) as described in Example 1, Step 2, using the foregoing ketal hydrogen oxalate instead of N-benzyl-N-(1,4-dioxaspiro [4.5]dec-8-yl)-N-methylamine. The hydrogen oxalate salt had mp 163–166° C. MS, ES$^+$, m/z=294 for (M+H)$^+$ of free base. (Found: C, 67.53; H, 6.56; N, 3.51. C$_{20}$H$_{23}$NO. 1.15 C$_2$H$_2$O$_4$ requires C, 67.48; H, 6.42; N, 3.53%).

3. E-4-[4-(N,N-Dibenzylamino)cyclohexylidene]but-2-enoic acid ethyl ester 1.6 Hydrogen Oxalate The title compound free base was obtained (12.2 g, 92%) as described in Example 1, Step 3 using 4-(N,N-dibenzylamino)cyclohexanone instead of 4-(N-benzyl-N-methylamino)cyclohexanone. The hydrogen oxalate salt had mp >50° C. MS, ES$^+$, m/z=390 for (M+H)$^+$, δ(360 MHz, d$_6$-DMSO) 1.21 (3H, t, J=7 Hz), 1.38–1.56 (2H, m), 1.74–1.86 (1H, t, J=15 Hz), 1.98–2.14 (3H, m), 2.30–2.35 (1H, d, J=12.6 Hz), 2.74–2.84 (1H, m), 2.90–2.96 (1H, d, J=13.5 Hz), 3.70 (4H, br s), 4.11 (2H, q, J=7 Hz), 5.87 (1H, d, J=15 Hz), 6.03 (1H, d, J=11.4 Hz), 7.20–7.40 (10H, m), 7.46 (1H, dd, J$_1$=11.6, J$_2$=15 Hz). (Found: C, 65.49; H, 6.60; N, 2.62. C$_{26}$H$_{31}$NO$_2$. 1.6C$_2$H$_2$O$_4$ requires C, 65.73; H, 6.46; N, 2.63%).

4. 4-[4-(N,N-Dibenzylamino)cyclohexyl]butyric acid ethyl ester

The title compound free base was obtained (12 g, 100%) as a mixture of cis and trans isomers as described in Example 1, Step 4 using the foregoing diene free base instead of E-4-[4 -(N-benzyl-N-methylamino) cyclohexylidene]but-2-enoic acid ethyl ester. MS, ES$^+$, m/z=394 for (M+H)$^+$ of free base. Thin layer chromatography on silica plates with ethyl acetate/hexane (1:4) gave R$_f$=0.76.

5. 4-[4-(N,N-Dibenzylamino)cyclohexyl]butan-1-ol

The title compound free base was obtained (9 g, 84%) as a mixture of cis and trans isomers as described in Example 1, Step 5 using the foregoing cyclohexylbutyric acid ethyl ester instead of cis-4-[4-(N-benzyl-N-methylamino) cyclohexyl]butyric acid ethyl ester. MS, ES$^+$, m/z=352 for (M+H)$^+$. Thin layer chromatography on silica plates with ethyl acetate/hexane (1:4) gave R$_f$=0.32.

6. Cis-[N,N-Dibenzyl-N-(4-(2-(5-(1,2,4-triazol-4-yl)-1H-indol-3-yl)ethyl)cyclohex-1-yl)]amine The foregoing alcohol (9 g, 0.026 mol) in dimethyl sulphoxide (75 ml) was treated with triethylamine (25 ml), then cooled (0° C.) followed by addition of sulphur trioxide pyridine complex (6.12 g, 0.038 mol) portionwise. The mixture was stirred for 1 hour while warming to ambient temperature followed by addition of sulphur trioxide pyridine complex (2 g, 0.012 mol), then stirred for a further 1 hour. Water (100 ml) was added and the mixture extracted with ethyl acetate (4 times). The combined organics were washed with brine (5 times), dried (sodium sulphate) and evaporated. The residue was purified by column chromatography on silica (short plug column) using hexane/ethyl acetate (2:1) to afford 4-[4-(N,N-dibenzylamino) cyclohexyl]butyraldehyde (8.5 g, 95%) as an orange oil. 4-[4-(N,N-Dibenzylamino)cyclohexyl]butyraldehyde (instead of cis-4-4-(N-benzyl-N-methylamino)cyclohexyl] butyraldehyde) was reacted with 4-(1,2,4-triazol-4-yl) phenylhydrazine hydrochloride, as in Example 1, Step 7, to give the title compound free base (2.7 g, 23%) as a mixture of cis and trans isomers. The cis isomer was obtained by recrystallisation from a mixture of methanolldiethyl ether. cis-isomer: MS, ES$^+$, m/z=490 for (M+H)$^+$, δ(360 MHz, CDCl$_3$) 1.38–1.43 (2H, m), 1.55–1.80 (9H, m), 2.50–2.58 (1H, m), 2.73 (1H, t, J=7 Hz), 3.64 (4H, s), 7.12–7.20 (4H, m), 7.25–7.29 (4H, m), 7.34–7.36 (4H, m), 7.45 (1H, d, J=8.7 Hz), 7.54 (1H, d, J=1.8 Hz), 8.28 (1H, br s, indole-NH), 8.45 (2H, s, 2×triazole-H). (Found: C, 75.76; H, 7.03; N, 13.52. C$_{32}$H$_{35}$N$_5$. 1.0H$_2$O requires C, 75.70; H, 7.35; N, 13.80%).

7. 4-[2-(5-(1,2,4-Triazol-4-yl)-1H-indol-3-yl)ethyl] cyclohexylamine

To a solution of the above dibenzyl amine (2.7 g, 5.5 mmol, mixture of cis/trans) in ethanol (150 ml) was added 10% palladium hydroxide on charcoal (4 g). The suspension was hydrogenated at 50 psi for 28 hours then the catalyst was filtered off. The solvent was evaporated and the residue was purified by column chromatography on alumina using ammonia/methanol/dichloromethane as eluent to afford the title compound as a mixture of cis and trans isomers (850 mg, 50%). MS, ES$^+$, m/z=310 for (M+H)$^+$, δ(360 MHz, d$_6$-DMSO) 0.90–1.02 and 1.70–1.84 (total of 1H, m), 1.17–1.59 (8H, m), 1.59–1.68 (2H, m), 2.71 (2H, t, J=7 Hz), 2.80–2.89 (1H, m), 7.21–7.33 (2H, m), 7.47 (1H, d, J=9 Hz), 7.75 (1H, d, J=2 Hz), 9.01 (2H, s), 11.09 (1H, broad s).

8. Cis-[N-(2-(RS)-1-Phenylprop-2-yl)-N-(4-(2-(5-(1,2,4-triazol-4-yl)-1H-indol-3-yl)ethyl)cyclohex-1-yl)]amine 1.5 Hydrogen Oxalate To the above cyclohexylamine (200 mg, 0.65 mmol) in dichloromethane (10 ml) was added phenylacetone (0.077 ml, 0.59 mmol), acetic acid (0.098 ml, 1.62 mmol) and sodium triacetoxyborohydride. The mixture was stirred for 3 days at room temperature, then the solvent was evaporated and the residue partitioned between 10% aqueous potassium carbonate and dichloromethane. The aqueous was re-extracted once with dichloromethane. The combined organics were dried (sodium sulphate), evaporated and the residue purified by preparative chromatography on silica using ammonia/methanol/dichloromethane as eluent to afford the title compound (165 mg, 56%). The hydrogen oxalate salt had mp >89° C. MS, ES$^+$, m/z=428 for (M+H)$^+$, δ(360 MHz, d$_6$-DMSO) 1.09 (3H, d, J=7 Hz), 1.49–1.88 (11H, m), 2.56–2.66 (1H, m), 2.73 (2H, t, J=7 Hz), 3.15–3.31 (2H, m), 3.46–3.57 (1H, m), 7.23–7.40 (7H, m), 7.48 (1H, d, J=8 Hz), 7.77 (1H, d, J=2 Hz), 8.50 (1H, broad s), 9.02 (2H, s), 11.10 (1H, s). (Found: C, 62.24; H, 6.36; N, 12.03. $C_{27}H_{33}N_5$. 1.5$C_2H_2O_4$. $H_2O$ requires C, 52.05; H, 6.59; N, 12.06%).

EXAMPLE 14

Cis-2-[N-Methyl-N-(4-(2-(5-(1,2,4-triazol-4-yl)-1H-indol-3-yl)ethyl)cyclohex-1-yl)amino]-1-(RS)-phenylethanol 1.55 Hydrogen Oxalate 1. Cis-2-[N-Methyl-N-(4-(2-(5-(1,2,4-triazol-4-yl)-1H-indol-3-yl)ethyl)cyclohex-1-yl)amino]-1-phenylethanone Cis-[N-Methyl-N-(4-(2-(5-(1,2,4-triazol-4-yl)-1H-indol-3-yl)ethyl)cyclohex-1-yl)]amine (250 mg, 0.77 mmol, Example 3, Step 1) in dimethylformamide (15 ml) was treated with potassium carbonate (106 mg, 0.77 mmol) and 2-bromoacetophenone (154 mg, 0.77 mmol) then stirred at room temperature for 3 hours. The solvent was evaporated and the residue partitioned between water and ethyl acetate. The organic layer was separated, and the aqueous was re-extracted with ethyl acetate. The combined organics were evaporated then the residue treated with ethanol to azeotrope residual water. The crude product was purified by column chromatography on silica (short plug column) using 3% methanol/dichloromethane to 5% methanol/dichloromethane to afford the title compound (150 mg, 44%). MS, ES$^+$, m/z=442 for (M+H)$^+$, δ(250 MHz, CDCl$_3$) 1.48–1.95 (11H, m,), 2.43 (3H, br s, N-Me), 2.64–2.86 (3H, m), 3.98 (2H, br s NCH$_2$COPh), 7.12 (2H, m), 7.42–7.59 (5H, m), 7.99–8.03 (2H, m), 8.41 (1H, br s, indole-NH) 8.48 (2H, s, 2×triazole-H).

2. Cis-2-[N-Methyl-N-(4-(2-(5-(1,2,4-triazol-4-yl)-1H-indol-3-yl)ethyl)cyclohex-1-yl)amino]-1-(RS)-phenylethanol 1.55 Hydrogen Oxalate The foregoing ketone (110 mg) dissolved in methanol (10 ml) and cooled (−20° C.) was treated with sodium borohydride (47 mg) and stirred under nitrogen for 3 hours whilst warming to room temperature. Water (10 ml) was added cautiously followed by dichloromethane. The organic layer was separated and aqueous re-extracted with dichloromethane (3 times). Combined organic layers were dried (potassium carbonate) and evaporated. The residue was purified by thin layer preparative chromatography on silica, eluting with a mixture of dichloromethanelmethanolfammonia (150:1:0.8) to afford the title compound free base as a pale yellow oil (70 mg, 63%). The hydrogen oxalate salt had mp >85° C. MS, ES$^+$, m/z=444 for (M+H)$^+$ of free base, δ(360 MHz, d$_6$-DMSO) 1.44–1.90 (11H, m), 2.66–2.72 (2H, m, CH$_2$-indole), 2.83 (3H, s, N-Me), 3.08–3.33 (3H, m), 4.98–5.04 (1H, m), 7.28–7.49 (8H, m), 7.76 (1H, d, J=2 Hz), 9.00 (2H, s, 2×triazole-H), 11.08 (1H, br s, indole-NH). (Found: C, 61.93; H, 6.61; N, 11.61. $C_{27}H_{33}N_5$. 1.55 $C_2H_2O_4$. 0.15$C_4H_{10}O$ requires C, 62.05; H, 6.38; N, 11.79%).

EXAMPLE 15

Cis-[N-Benzl-N-(4-(2-(5-(1,2,4-triazol-4-yl)-1H-indol-3-yl)ethyl)cyclohex-1-yl)]amine 2 Hydrogen Oxalate To a solution of 4-[2-(5-(1,2,4-triazol-4-yl)-1H-indol-3-yl)ethyl]cyclohexylamine from Example 13, Step 7 (100 mg, 0.32 mmol) in methanol (10 ml) was added benzaldehyde (0.029 ml, 0.29 mmol), acetic acid (0.077 ml, 1.28 mmol) and sodium cyanoborohydride (20.3 mg, 0.32 mmol). The solution was stirred for 18 hours at room temperature, quenched with 10% aqueous potassium carbonate and evaporated to dryness. The residue was partitioned between 10% aqueous potassium carbonate and dichloromethane. The organic layer was decanted and the aqueous re-extracted with dichloromethane. The combined organics were dried (sodium sulphate) and evaporated, and the residue purified by preparative chromatography on silica using ammonia/methanol/dichloromethane as eluent to afford the title compound (90 mg, 70%) and its trans isomer (10 mg, 8%). The title compound hydrogen oxalate salt had MS, ES$^+$, m/z=400 for (M+H)$^+$, δ(360 MHz. d$_6$-DMSO) 1.43–1.86 (11H, m), 2.72 (2H, t, J=7 Hz), 3.03–3.12 (1H, m), 4.17 (2H, s), 7.23–7.31 (2H, m), 7.37–7.52 (7H, m), 7.75 (1H, d, J=2 Hz), 9.01 (2H, s), 11.10 (1H, br s). (Found: C, 59.88; H, 5.91; N, 12.08. $C_{25}H_{29}N_5$. 2$C_2H_2O_4$ requires C, 60.09; H, 5.74; N, 12.08%).

EXAMPLE 16

Cis-[N-(2-(RS)-1,2,3,4-Tetrahydronaphth-2-yl)-N-(4-(2-(5-(1,2,4-triazol-4-yl)-1H-indol-3-yl)ethyl) cyclohex-1-yl)]amine 1.5 Hydrogen Oxalate The title compound free base was obtained (120 mg, 42%) as described in Example 4 using cis-4-[2-(5-(1,2,4-triazol-4-yl)-1H-indol-3-yl)ethyl]cyclohexylamine (Example 13, Step 7) instead of cis-[N-methyl-N-(4-(2-(5-(1,2,4-triazol-4-yl)-1H-indol-3-yl)ethyl)cyclohex-1-yl)]amine (Example 3, Step 1); and β-tetralone instead of 3-fluorobenzaldehyde. The hydrogen oxalate had mp >120° C. MS, ES$^+$, m/z=440 for (M+H)$^+$ of free base. (Found: C, 64.59; H, 6.57; N, 12.14. $C_{28}H_{33}N_5$. 1.5$C_2H_2O_4$ requires C, 64.79; H, 6.31; N, 12.19%).

EXAMPLE 17

Cis-[N-Methyl-N-(2-(RS)-1,2,3,4-tetrahydronaohth-2-yl)-N7-(4-(2-(5-(1,2,4-triazol-4-yl)-1H-indol-3-yl)ethyl)cyclohex-1-yl)]amine 1.3 Hydrogen Oxalate The title compound free base was obtained (90 mg, 84%) as described in Example 7, Step 2 using cis-[N-(2-(RS)-1,2,3,4-tetrahydronaphth-2-yl)-N-(4-(2-(5-(1,2,4-triazol-4-yl)-1H-indol-3-yl)ethyl)cyclohex-1-yl)]amine (Example 16) instead of cis-[N-methyl-N-(4-(3-(5-(1,2,4-triazol-4-yl)-1H-indol-3-yl)propyl)cyclohex-1-yl)]amine formate (Example 7, Step 1); and formaldehyde instead of 2-(RS)-phenylpropionaldehyde. The reaction time was 2 days and no further quantities of aldehyde and sodium cyanoborohydride needed. The hydrogen oxalate had mp >115° C. MS, ES$^+$, m/z=454 for (M+H)$^+$ of free base. (Found: C, 66.49; H, 7.03; N, 12.36. $C_{29}H_{35}N_5$. 1.3$C_2H_2O_4$. 0.15$C_4H_{10}O$ requires C, 66.48; H, 6.78; N, 12.04%).

EXAMPLE 18

Cis-[N-(2-(RS)-Phenylnrolyl)-N-(4-(2-(5-(1,2,4-triazol-4-yl)-1H-indol-3-yl)ethyl)cyclohex-1-yl)] amine 1.5 Hydrogen Oxalate The title compound was prepared using the procedure described in Example 15 using 2-phenylpropionaldehyde instead of benzaldehyde. The title compound had mp >90° C. MS, ES$^+$, m/z=428 for (MACH)$^+$, δ(360 MHz, d$_6$-DMSO) 1.26 (3H, d, J=7 Hz), 1.40–1.83 (1H, m), 2.69

(2H, t, J=7 Hz), 3.00–3.20 (4H, m), 7.21–7.39 (7H, m), 7.47 (1H, d, J=8 Hz), 7.75 (1H, d, J=2 Hz), 8.4 (1H, br s), 9.01 (2H, s), 11.09 (1H, s). (Found: C, 62.39; H, 6.48; N, 12.11. $C_{27}H_{33}N_5 \cdot 1.5C_2H_2O_4 \cdot H_2O$ requires C, 62.05; H, 6.60; N, 12.07%).

EXAMPLE 19

Cis-[N-Methyl-N-(2-(RS)-1-phenylprop-2-yl)-N-(4-(2-(5-(1,2,4-triazol-4-yl)-1H-indol-3-yl)ethyl) cyclohex-1-yl)]amine 2 Hydrogen Oxalate The title compound was obtained following the procedure described in Example 15 using formaldehyde (instead of benzaldehyde) and the secondary amine from Example 13, Step 8 (instead of the primary amine from Example 13, Step 7). The hydrogen oxalate had mp >80° C. MS, ES$^+$, m/z=442 for (M+H)$^+$, δ(360 MHz, d$_6$-DMSO) 1.11 (3H, d, J=7 Hz), 1.48–1.89 (11H, mn), 2.62–2.79 (1H, m), 2.68 (3H, s), 2.73 (2H, t, J=7 Hz), 3.10–3.27 (2H, mn), 3.60–3.72 (1H, mn), 7.19–7.36 (7H, mn), 7.48 (1H, d, J=8 Hz), 7.71 (1H, d, J=2 Hz), 8.87 (2H, s), 10.87 (1H, s). (Found C, 61.59; H, 6.38; N, 11.36. $C_{28}H_{35}N_5 \cdot 2C_2H_2O_4$ requires C, 61.82; H, 6.32; N, 11.27%).

EXAMPLE 20

Trans-2(R)-Phenyl-2-[4-(2-(5-(1,2,4-triazol-4-yl)-1H-indol-3-yl)ethyl)cyclohexylamino]ethanol 2 Hydrogen Oxalate 1. 1,4-Dioxaspiro[4.5]decan-8-ol A stirred, cooled (5° C.) solution of 1,4-dioxaspiro[4.5] decan-8-one (20 g, 0.128 mol) in ethanol (250 ml) was treated with sodium borohydride (7.3 g, 0.192 mol) in portions over 20 minutes. The reaction mixture was stirred at 5° C. for 1 hour then at room temperature for 1 hour. Water (20 ml) was added and the mixture was stirred vigorously for 10 minutes then concentrated in vacuo. The residue was partitioned between water (100 ml) and ethyl acetate (100 ml). The organic layer was separated and the aqueous re-extracted with ethyl acetate (100 ml). The combined organics were dried (sodium sulphate) then evaporated to give the title alcohol as a colourless oil (17.1 g, 84%). MS ES$^+$, m/z=159 for (M+H)$^+$; δ(360 MHz, CDCl$_3$) 1.52–1.71 (4H, m), 1.78–1.92 (4H, m), 3.76–3.83 (1H, m), 3.91–3.94 (4H, m).

2. 8-Benzyloxy-1,4-dioxaspiro[4.5]decane

A stirred solution of the foregoing alcohol (17 g, 0.107 mol) in anhydrous tetrahydrofuran (170 ml), under an atmosphere of nitrogen, was treated with sodium hydride (4.7 g of a 55% oil dispersion, 0.107 mol) in portions over 20 minutes. After stirring for 30 minutes the reaction mixture was treated with benzyl bromide (12.7 ml, 0.107 mol), dropwise. The reaction mixture was stirred at room temperature for 18 hours, treated with water (2 ml), then stirred for 30 minutes. The mixture was filtered, the filtrate evaporated, re-dissolved in diethyl ether (200 ml) and washed with water (2×200 ml). The organic layer was dried (sodium sulphate) then evaporated to give a gum which was purified by column chromatography on silica using ethyl acetate/n-hexane (1:2) to give the title product as a colourless oil (24.8 g, 93%). MS, ES$^+$, m/z=249 for (M+H)$^+$; δ(360 MHz, CDCl$_3$) 1.50–1.60 (2H, m), 1.75–1.90 (6H, m), 3.50–3.54 (1H, m), 3.90–3.98 (4H, m), 4.52 (2H, s), 7.23–7.36 (5H, m).

3. 4-Benzyloxycyclohexanone

The foregoing acetal (23 g, 0.093 mol) in tetrahydrofuran (250 ml) was treated with 5M hydrochloric acid (150 ml) and stirred at room temperature for 4 hours. The tetrahydrofuran was evaporated, the aqueous basified to pH=7 with 40% sodium hydroxide solution, then extracted with ethyl acetate (3×200 ml). The combined organics were washed with brine (200 ml), dried (sodium sulphate) then evaporated to dryness. The residue was purified on a plug silica column using ethyl acetate/n-hexane (1:3) to give the title ketone as a colourless oil (16.5 g, 87%). MS, ES$^+$, m/z=205 for (M+H)$^+$; δ(360 MHz, CDCl$_3$) 1.94–2.02 (2H, m), 2.12–2.18 (2H, m), 2.22–2.32 (2H, m), 2.58–2.68 (2H, m), 3.82–3.84 (1H, m), 4.60 (2H, s), 7.29–7.37 (5H, m).

4. E-4-(4-Benzyloxycyclohexylidene)but-2-enoic acid ethyl ester

A stirred, cooled (−78° C.) solution of triethyl phosphonocrotonate (28.3 ml, 0.128 mol) in anhydrous tetrahydrofuran (350 ml), under a nitrogen atmosphere, was treated with a 0.5M toluene solution of potassium bis (trimethylsilyl)amide (240 ml, 0.12 mol) dropwise over 30 minutes. The dark orange solution was stirred at −78° C. for 5 hours then treated slowly with a solution of 4-benzyloxycyclohexanone (16.3 g, 0.08 mol) in anhydrous tetrahydrofuran (50 ml). The reaction mixture was stirred at −78° C. for 2 hours then stirred whilst warming to room temperature overnight. The mixture was quenched with saturated ammonium chloride solution (250 ml) then the tetrahydrofuran was evaporated and the aqueous was extracted with ethyl acetate (3×200 ml). The combined organics were washed with brine, dried (sodium sulphate) then evaporated to dryness. The residue was purified by column chromatography on silica using ethyl acetate/n-hexane (1:5) to afford the diene as a colourless oil (22.0 g, 92%). MS, ES$^+$, m/z=301 for (M+H)$^+$; δ(250 MHz, CDCl$_3$) 1.30 (3H, t, J=7 Hz), 1.62–1.80 (2H, m), 1.84–2.00 (2H, m), 2.06–2.34 (2H, m), 2.40–2.54 (1H, m), 2.64–2.80 (1H, m), 3.59–3.66 (1H, m), 4.20 (2H, q, J=7 Hz), 5.81 (1H, d, J=15 Hz), 5.97 (1H, d, J=12 Hz), 7.26–7.37 (5H, m), 7.60 (1H, dd, $J_1$=12, $J_2$=15 Hz).

5. 4-(4-Hydroxycyclohexyl)butyric acid ethyl ester

To a solution of the foregoing ester (21.9 g, 73 mmol) in ethanol (100 ml) was added 10% palladium on carbon (2 g). The suspension was hydrogenated at 50 psi for 3 hours then the catalyst was filtered off. The filtrate was evaporated to afford the title compound as a mixture of cis and trans isomers (15.5 g, 99%). MS, ES$^+$, m/z=215 for (M+H)$^+$, δ(360 MHz, CDCl$_3$) 0.88–1.03 and 1.12–1.84 and 1.92–2.02 (total of 13H, m), 1.26 (3H, t, J=7 Hz), 2.28 and 2.29 (total of 2H, t, J=4 Hz), 3.49–3.60 and 3.90–3.99 (total of 1H, m), 4.12 (2H, q, J=7 Hz).

6. 4-[4-(tert-Butyldimethylsilanyloxy)cyclohexyl]butyric acid ethyl ester

To a mixture of tert-butyldimethylsilyl chloride (12 g, 80.3 mmol) and imidazole (7.5 g, 109.5 mmol) in dimethylformamide (55 ml) was added a solution of the foregoing ester (15.3 g, 72 mmol) in dimethylformamide (5 ml). The solution was stirred at room temperature for 4 hours then quenched with water and diluted with ethyl acetate. The organic layer was decanted, washed with water, dried (sodium sulphate) and evaporated to give the title compound as a mixture of cis and trans isomers (22 g, 92%). MS, ES$^+$, m/z=329 for (M+H)$^+$, δ(250 MHz, CDCl$_3$) 0.01 (6H, s), 0.86 (9H, s), 1.10–1.90 (13H, m), 1.23 (3H, t, J=7 Hz), 2.24 and 2.25 (total of 2H, t, J=7 Hz), 3.40–3.55 and 3.83–3.92 (total of 1H, m), 4.10 (2H, q, J=7 Hz).

7. 4-[4-(tert-Butyldimethylsilanyloxy)cyclohexyl]butan-1-ol

To a solution of the above protected alcohol (22 g, 67 mmol) in dry toluene (350 ml), under nitrogen at 0° C., was added diisobutylaluminium hydride in toluene (130 ml of a 1.5 M solution). The solution was stirred at room temperature for 4 hours and cooled down to 0° C. before carefully adding methanol (90 ml) and 10% aqueous potassium carbonate (200 ml). The mixture was evaporated to dryness and the residue partitioned between water and ethyl acetate. After filtering through hyflo the organic layer was decanted, washed with brine, dried (sodium sulphate) and evaporated to afford the title compound as a mixture of cis and trans isomers (16 g, 83%). MS, ES$^+$, m/z=287 for (M+H)$^+$, δ(360 MHz, CDCl$_3$) 0.01 (6H, s), 0.86 (9H, s), 1.10–2.02 (13H, m), 3.42–3.57 and 3.84–3.92 (total of 1H, m), 3.62 (2H, t, J=7 Hz).

8. 4-[4-(tert-Butyldimethylsilanyloxy)cyclohexyl]butyraldehyde

To a solution of the foregoing butanol (16 g, 56 mmol) in dichloromethane (800 ml), under nitrogen, was added N-methylmorpholine-N-oxide (20.5 g, 175 mmol). After stirring for 15 minutes at room temperature tetrapropylammonium perruthenate (1.2 g, 3.4 mmol) was added. The black solution was stirred for 24 hours at room temperature before being filtered through a short silica plug column eluting with dichloromethane. The solvent was evaporated to afford the title aldehyde as a mixture of cis and trans isomers (7 g, 44%). MS, ES$^+$, m/z=285 for (M+H)$^+$, δ(360 MHz, CDCl$_3$) 0.01 (6H, s), 0.86 (9H, s), 1.12–1.88 (13H, m), 2.37 and 2.38 (total of 2H, t, J=7 Hz), 3.42–3.54 and 3.86–3.90 (total of 1H, m).

9. 4-[2-(5-(1,2,4-triazol-4-yl)-1H-indol-3-yl)ethyl]cyclohexanol

A stirred mixture of 4-(1,2,4-triazol-4-yl)phenylhydrazine hydrochloride (930 mg, 3.5 mmol) in ethanol/water (25 ml, 4:1), under nitrogen, was slowly treated with a solution of 4-[4-(tert-butyldimethylsilanyloxy)cyclohexyl]butyraldehyde (1 g, 3.5 mmol) in ethanol (5 ml). The reaction mixture was heated at 140° C. for 18 hours in a sealed tube, cooled and evaporated. The residue was purified by column chromatography on silica using methanol/dichloromethane as eluent to afford the title compound as a mixture of cis and trans isomers (1 g, 92%). MS, ES$^+$, m/z=311 for (M+H)$^+$, δ(250 MHz, d$_6$-DMSO) 1.07–1.88 (11H, m), 2.71 (2H, t, J=7 Hz), 3.70–3.78 (1H, m), 4.26 (1H, d, J=3 Hz), 7.21–7.32 (2H, m), 7.47 (1H, d, J=9Hz), 7.76 (1H, d, J=2Hz), 9.02 (2H, s), 11.10 (1H, br s).

10. 4-[2-(5-(1,2,4-triazol-4-yl)-1H-indol-3-yl)ethyl]cyclohexanone

To a solution of the foregoing alcohol (950 mg, 3 mmol) in dimethyl sulphoxide (30 ml), under nitrogen, was added triethylamine (3 ml. 21.5 mmol) and sulphur trioxide pyridine complex (1.8 g, 11.3 mmol) in 3 portions. The yellow solution was stirred at room temperature for 3½ hours then 10% aqueous potassium carbonate was added and the solid filtered off. The filtrate was extracted twice with ethyl acetate. The combined organics were washed with brine (3×), water (3×), dried (sodium sulphate) and evaporated. The residue was purified by column chromatography on silica using 2% methanol in dichloromethane as eluent to afford the title cyclohexanone (430 mg, 46%). MS, ES$^+$, m/z=309 for (M+H)$^+$, δ(250 MHz, d$_6$-DMSO) 1.31–1.52 (2H, m), 1.63–1.88 (3H, m), 2.03–2.48 (6H, m), 2.78 (2H, t, J=7 Hz), 7.27–7.35 (2H, m), 7.47 (1H, d, J=2 Hz), 7.79 (1H, d, J=2 Hz), 9.03 (1H, s), 11.09 (1H, br s).

11. Trans-2(R)-Phenyl-2-[4-(2-(5-(1,2,4-triazol-4-yl)-1H-indol-3-yl)ethyl)cyclohexylamino]ethanol 2 Hydrogen Oxalate To a solution of the foregoing cyclohexanone (200 mg, 0.65 mmol) in methanol (15 ml) was added (R)-2-phenylglycinol (133 mg, 0.97 mmol), glacial acetic acid (0.15 ml, 2.6 mmol) and sodium cyanoborohydride (61 mg, 0.97 mmol). The solution was stirred at room temperature overnight, quenched with 10% aqueous potassium carbonate and evaporated to dryness. The residue was partitioned between water and dichloromethane. The organic layer was decanted and the aqueous re-extracted once with dichloromethane. The combined organics were dried (sodium sulphate), evaporated and purified by column chromatography on silica, using ammonia/methanol/dichloromethane (0.5/5/95) as eluent, to afford the cis isomer (70 mg, 25%) and the trans isomer (140 mg, 50%). cis isomer free base: MS, ES$^+$, m/z=430 for (M+H)$^+$, δ(360 MHz, CDCl$_3$) 1.40–1.62 (8H, m), 1.63–1.75 (3H, m), 2.66–2.72 (1H, m), 2.75 (2H, t, J=7 Hz), 3.43–3.51 (1H, m), 3.68 (1H, dd, J=5 and 11 Hz), 3.86 (1H, dd, J=5 and 9 Hz), 7.09–7.17 (2H, m), 7.24–7.32 (2H, m), 7.32–7.39 (1H, m), 7.47 (1H, d, J=9 Hz), 7.53 (1H, d, J=2 Hz), 8.47 (2H, s), 8.64 (1H, br s). The title compound had mp >125° C. MS, ES$^+$, m/z=430 for (M+H)$^+$, δ(360 MHz, d$_6$-DMSO) 0.70–0.97 (2H, m), 1.14–1.57 (5H, m), 1.79–1.90 (2H, m), 1.95–2.11 (2H, m), 2.68 (2H, t, J=7 Hz), 3.60–3.83 (3H, m), 4.23–4.30 (1H, m), 4.36–4.46 (1H, m), 7.21–7.60 (8H, m), 7.72 (1H, d, J=2 Hz), 8.99 (2H, s), 11.07 (1H, s). (Found C, 59.10; H, 6.30; N, 10.99. C$_{26}$H$_{31}$N$_5$O. 2C$_2$H$_2$O$_4$. 0.2C$_4$H$_{10}$O requires C, 59.24; H, 5.97; N, 11.22%).

EXAMPLE 21

Trans-2(S)-Phenyl-2-[4-(2-(5-(1,2,4-triazol-4-yl)-1H-indol-3-yl)ethyl)cyclohexylamino]ethanol 2 Hydrogen Oxalate The title compound and its cis isomer were obtained as described in Example 20, Step 11 using (S)-2-phenylglycinol. cis isomer free base: MS, ES$^+$, m/z=430 for (M+H)$^+$, δ(250 MHz, CDCl$_3$) 1.40–1.62 (8H, m), 1.62–1.76 (3H, m), 2.67–2.82 (1H, m), 2.75 (2H, t, J=7 Hz), 3.49 (1H, t, J=11 Hz), 3.67 (1H, dd, J=5 and 11 Hz), 3.90 (1H, dd, J=5 and 9 Hz), 7.10–7.20 (2H, m), 7.23–7.42 (5H, m), 7.47 (1H, d, J=9H), 7.54 (1H, d, J=2 Hz), 8.30 (1H, br s), 8.49 (2H, s). The title compound had mp >125° C. MS, ES$^+$, m/z=430 for (M+H)$^+$, δ(360 MHz, d$_6$-DMSO) 0.70–0.97 (2H, m), 1.14–1.30 (1H, m), 1.30–1.56 (4H, m), 1.78–1.89 (2H, m), 1.97–2.10 (2H, m), 2.67 (2H, t, J=7 Hz), 3.62–3.86 (3H, m), 4.24–4.30 (1H, m), 4.40–4.51 (1H, m), 7.20–7.60 (8H, m), 7.72 (1H, d, J=7 Hz), 8.99 (2H, s), 11.07 (1H, br s). (Found C, 58.47; H, 6.21; N, 10.64. C$_{26}$H$_{31}$N$_5$O. C$_2$H$_2$O$_4$. 0.3C$_4$H$_{10}$O. 0.5H$_2$O requires C, 58.47; H, 6.13; N, 10.93%).

EXAMPLE 22

Cis-2-[N-Methyl-N-[4-(2-(5-(1,2,4-triazol-4-yl)-1H-indol-3-yl)ethyl)cyclohexyl]amino]-2(R)-phenylethanol 1.75 Hydrogen Oxalate The title compound was obtained following the reductive amination procedure described in Example 20 (Step 11) using the cis isomer from Example 20 (Step 11) and formaldehyde. The hydrogen oxalate had mp >133° C. MS, ES$^+$, m/z=444 for (M+H)$^+$, δ(360 MHz, d$_6$-DMSO) 1.28–1.48 (2H, m), 1.56–1.88 (9H, m), 2.63 (3H, s), 2.69 (2H, t, J=7 Hz), 3.04–3.20 (1H, m), 3.88–4.00 (1H, m), 4.00–4.08 (1H, m), 4.32–4.42 (1H, m), 4.48–4.56 (1H, m), 7.24–7.61 (8H, m), 7.75 (1H, d, J=2 Hz), 9.01 (2H, s), 11.10 (1H, br s). (Found: C, 630.22; H, 6.25; N, 11.81. C$_{27}$H$_{33}$N$_5$O. 1.75C$_2$H$_2$O$_4$. 0.25H$_2$O requires C, 60.48; H, 6.16; N, 11.56%).

EXAMPLE 23

Cis-2-[N-Methyl-N-[4-(2-(5-(1,2,4-triazol-4-yl)-1H-indol-3-yl)ethyl)cyclohexyl]amino]-2(S)-phenylethanol 1.25 Hydrogen Oxalate The title compound was obtained following the reductive amination procedure described in Example 20 (Step 11)

using the cis isomer from Example 21 and formaldehyde. The hydrogen oxalate had mp >143° C. MS, ES+, m/z=444 for (M+H)+, δ(360 MHz, d6-DMSO) 1.28–1.45 (2H, m), 1.57–1.78 (9H, m), 2.50 (3H, s), 2.68 (2H, t, J=7 Hz), 2.91–3.12 (1H, m), 3.80–4.10 (3H, m), 4.39 (1H, br s), 7.26–7.55 (8H, m), 7.75 (1H, d, J=2 Hz), 9.00 (2H, s), 11.08 (1H, br s). (Found: C, 63.43; H, 6.85; N, 12.17. $C_{27}H_{33}N_5O$. $1.25C_2H_2O_4$. $0.25H_2O$ requires C, 63.20; H, 6.47; N, 12.49%).

EXAMPLE 24

Trans-2-[N-Methyl-N-[4-(2-(5-(1,2,4-triazol-4-yl)-1H-indol-3-yl)ethyl)cyclohexyl]amino]-2(S)-phenylethanol 3 Hydrogen Oxalate The title compound was obtained following the reductive amination procedure described in Example 20 (Step 11) using the trans isomer from Example 21 and formaldehyde. The hydrogen oxalate had mp >88° C. MS, ES+, m/z=444 for (M+H)+, δ(360 MHz, d6-DMSO) 0.90–1.02 (2H, m), 1.09–1.32 (1H, m), 1.34–1.60 (4H, m), 1.84–2.05 (4H, m), 2.61 (3H, s), 2.69 (2H, t, J=7 Hz), 3.00–3.14 (1H, m), 3.82–4.04 (2H, m), 4.21–4.51 (1H, m), 4.38–4.50 (1H, m), 7.22–7.60 (8H, m), 7.73 (1H, d, J=2 Hz), 9.00 (2H, s), 11.07 (1H, br s). (Found: C, 59.20; H, 6.72; N, 11.14. $C_{27}H_{33}N_5O$. $3C_2H_2O_4$. $1.5H_2O$ requires C, 59.49; H, 6.49; N, 11.56%).

What is claimed is:

1. A compound of formula I, or a pharmaceutically acceptable salt thereof:

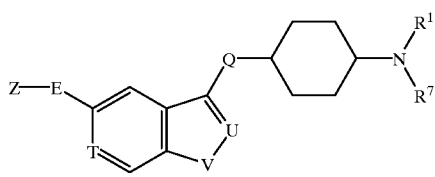

(I)

wherein

Z represents an optionally substituted triazole wherein the substituent is selected from C1–6 alkyl, C2–6 alkenyl, C2–6 alkynyl, C3–7 cycloalkyl, aryl aryl(C1–6) alkyl, C1–6 alkoxy, C1–6 alkylthio, amino, C1–6 alkylamino, di(C1–6)alkyamino halogen, cyano and trifluoromethyl E represents a chemical bond or a straight or branched alkylene chain containing from 1 to 4 carbon atoms;

Q represents a straight or branched alkylene chain containing from 1 to 6 carbon atoms, optionally substituted in any position by one or more substituents selected from fluoro and hydroxy;

T represents CH;

U represents C—$R^2$;

V represents N—$R^3$;

$R^1$ represents aryl($C_{1-6}$)alkyl or tetrahydronaphthyl, any of which groups may be optionally substituted wherein the substituent is selected from halogen, cyano, trifluoromethyl, hydroxy, keto,C1–6 alkoxy, C1–6 alkylthio, C2–6 alkoxycarbonyl, C2–6 alkylcarbonyl, C1–6 alkylsulphonyl, arylsulphonyl, amino, C1–6 alkylamino, di(C1–6)alkylamino, di(C1–6) alkylaminomethyl, C2–6 alkylcarbonylamino, arylcarbonylamino, C2–6 alkoxycarbonylamino, N—(C1–6)alkyl-N—(C2–6) alkoxycarbonylamino, C1–6 alkylsulphonylamino, arylsulphonylamino, C1–6 alkylsulphonylaminomethyl, aminocarbonylamino, C1–6 alkylaminocarbonylamino, di(C1–6) alkylaminocarbonylamino, mono or diarylaminocarbonylamino, aminocarbonyl, C1–6 alkylaminocarbonyl, di(C1–6)alkylaminocarbonyl, aminosulphonyl, C1–6 alkylaminosulphonyl, di(C1–6) alkylaminosulphonyl, aminosulphonylmethyl, C1–6 alkylaminosulphonylmethyl and di(C1–6) alkylaminosulphonylmethyl; and $R^2$, $R^3$ and $R^7$ independently represent hydrogen or $C_{1-6}$ alkyl.

2. A compound of formula I as defined in claim 1, or a pharmaceutically acceptable salt thereof, wherein $R^1$ represents aryl($C_{1-6}$)alkyl which may be optionally substituted.

3. A compound as claimed in claim 1 represented by formula II, and pharmaceutically acceptable salts thereof:

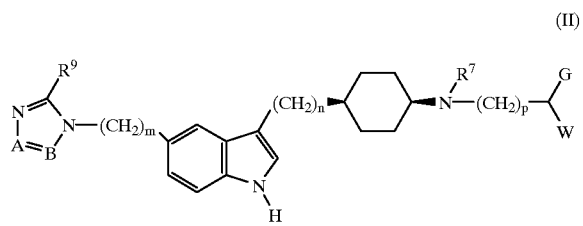

(II)

wherein m is zero, 1, 2 or 3;

n is 2, 3 or 4;

p is zero, 1 or 2;

A represents nitrogen and B represents C—$R^{10}$; or

A represents CH and B represents nitrogen;

$R^7$ is as defined in claim 1;

$R^9$ and $R^{10}$ independently represent hydrogen, $C_{1-6}$ alkyl, $C_{2-6}$ alkenyl, $C_{3-7}$ cycloalkyl, aryl, aryl($C_{1-6}$)alkyl, $C_{1-6}$alkoxy, $C_{1-6}$ alkylthio amino, $C_{1-6}$ alkylamino, di($C_{1-6}$)alkylamino, halogen, cyano or trifluoromethyl;

G represents hydrogen, hydroxy, $C_{1-3}$ alkyl or hydroxy ($C_{1-3}$)alkyl; and W represents a group of formula (Wa):

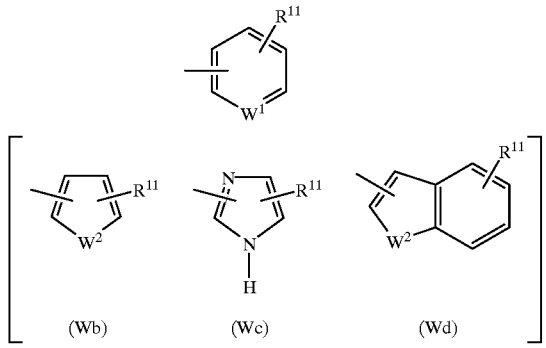

in which $W^1$ represents CH; and $R^{11}$ represents hydrogen, halogen, cyano, trifluoromethyl, $C_{1-6}$ alkoxy, $C_{2-6}$alkylcarbonyl, amino, $C_{1-6}$ alkylamino, di($C_{1-6}$)alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl or $C_{1-6}$ alkylaminosulphonylmethyl.

4. The compound of claim 1 selected from:

cis-[N-benzyl-N-methyl-N-(4-(2-(5-(1,2,4-triazol-4-yl)-1H-indol-3-yl)ethyl)-cyclohex-1-yl)]amine;

cis-[N-benzyl-N-methyl-N-(4-(3-(5-(1,2,4-triazol-4-yl)-1H-indol-3-yl)-propyl)cyclohex-1-yl)]amino;

cis-[N-methyl-N-(1-phenylethyl)-N-(4-(2-(5-(1,2,4-triazol-4-yl)-1H-indol-3-yl)ethyl)cyclohex-1-yl)]amine;

cis-[N-(3-fluorobenzyl)-N-methyl-N-(4-(2-(5-(1,2,4-triazol-4-yl)-1H-indol-3-yl)ethyl)cyclohex-1-yl)]amine;

cis-[N-methyl-N-(2-(RS)-phenylpropyl)-N-(4-(2-(5-(1,2,4-triazol-4-yl)-1H-indol-3-yl)ethyl)cyclohex-1-yl)]amine;

cis-[N-methyl-N-(2-(RS)-phenylpropyl)-N-(4-(3-(5-(1,2,4-triazol-4-yl)-1H-indol-3-yl)propyl)cyclohex-1-yl)]amine;

cis-[N-(2-(RS)-(4-fluorophenyl)propyl)-N-methyl-N-(4-(2-(5-(1,2,4-triazol-4-yl)-1H-indol-3-yl)ethyl)cyclohex-1-yl)]amine;

and pharmaceutically acceptable salts thereof.

5. The compound of claim 1 selected from:

cis-[N-methyl-N-(2-phenylethyl)-N-(4-(2-(5-(1,2,4-triazol-4-yl)-1H-indol-3-yl)ethyl)cyclohex-1-yl)]amine;

cis-[N-(2-(RS)-1-phenylprop-2-yl)-N-(4-(2-(5-(1,2,4-triazol-4-yl)-1H-indol-3-yl)ethyl)cyclohex-1-yl)]amine;

cis-2-[N-methyl-N-(4-(2-(5-(1,2,4-triazol-4-yl)-1H-indol-3-yl)ethyl)cyclohex-1-yl)amino]-1-(RS)-phenylethanol;

cis-[N-benzyl-N-(4-(2-(5-(1,2,4-triazol-4-yl)-1H-indol-3-yl)ethyl)cyclohex-1-yl)]amine;

cis-[N-(2-(RS)-1,2,3,4-tetrahydronaphth-2-yl)-N-(4-(2-(5-(1,2,4-triazol-4-yl)-1H-indol-3-yl)ethyl)cyclohex-1-yl)]amine;

cis-[N-methyl-N-(2-(RS)-1,2,3,4-tetrahydronaphth-2-yl)-N-(4-(2-(5-(1,2,4-triazol-4-yl)-1H-indol-3-yl)ethyl)cyclohex-1-yl)]amine;

cis-[N-(2-(RS)-phenylpropyl)-N-(4-(2-(5-(1,2,4-triazol-4-yl)-1H-indol-3-yl)ethyl)cyclohex-1-yl)]amine;

cis-[N-methyl-N-(2-(RS)-1-phenylprop-2-yl)-N-(4-(2-(5-(1,2,4-triazol-4-yl)-1H-indol-3yl)ethyl)cyclohex-1-yl)]amine;

trans-2(R)-phenyl-2-[4-(2-(5-(1,2,4-triazol-4-yl)-1H-indol-3-yl)ethyl)cyclohexy(amino]ethanol;

trans-2(S)-phenyl-2-[4-(2-(5-(1,2,4-triazol-4-yl)-1H-indol-3-yl)ethyl)cyclohexylamino]ethanol;

cis-2-[N-methyl-N-[4-(2-(5-(1,2,4-triazol-4-yl)-1H-indol-3-yl)ethyl)cyclohexyl]amino]-2(R)-phenylethanol;

cis-2-[N-methyl-N-[4-(2-(5-(1,2,4-triazol-4-yl)-1H-indol-3-yl)ethyl)cyclohexyl]amino]-2(S)-phenylethanol;

trans-2-[N-methyl-N-[4-(2-(5-(1,2,4-triazol-4-yl)-1H-indol-3-yl)ethyl)cyclohexylamino]-2(S)-phenylethanol;

and pharmaceutically acceptable salts thereof.

6. A pharmaceutical composition comprising a compound of formula I as defined in claim 1 or a pharmaceutically acceptable salt thereof in association with a pharmaceutically acceptable carrier.

7. A pharmaceutical composition comprising a compound of claim 4 or a pharmaceutically acceptable salt thereof association with a pharmaceutically acceptable carrier.

8. A pharmaceutical composition comprising a compound of claim 5 or a pharmaceutically acceptable salt thereof association with a pharmaceutically acceptable carrier.

9. A method for the treatment of migraine, cluster headache, chronic paroxysmal hemicrania, headache associated with vascular disorders, tension headache, and pediatric migraine, which method comprises administering to a patient in need of such treatment an effective amount of a compound of formula I as defined in claim 1 or a pharmaceutically acceptable salt thereof.

10. A process for the preparation of a compound as claimed in claim 1, which comprises:

attachment of the $R^1$ moiety to a compound of formula XIV:

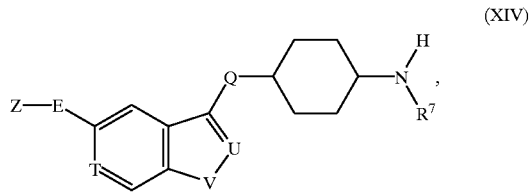

(XIV)

wherein the $R^1$ moiety is attached to the compound of formula XIV by the reductive alkylation of a compound of formula XIV and the ketone or aldehyde precursor that yields a compound of formula I in the presence of a reducing agent, wherein Z, E, Q, T, U, V, $R^1$ and $R^2$ are as defined in claim 1; and optionally converting a compound of formula I initially obtained into a further compound of formula I by conventional methods.

* * * * *